(12) United States Patent
Guilford et al.

(10) Patent No.: US 8,679,530 B2
(45) Date of Patent: Mar. 25, 2014

(54) LIPOSOMALLY ENCAPSULATED REDUCED GLUTATHIONE, INCLUDING WITH OTHER PHARMACOLOGIC PREPARATION, CAPABLE OF ADMINISTRATION AS AN ORAL, TOPICAL, INTRAORAL OR TRANSMUCOSAL, PREPARTION, FOR REVERSAL AND PREVENTION OF OXIDATION OF CHOLESTEROL AND OF LOW DENSITY LIPOPROTEIN

(75) Inventors: F. Timothy Guilford, Palo Alto, CA (US); Brooke Schumm, III, Ellicott City, MD (US)

(73) Assignee: Your Energy Systems, LLC, Palo Alto, CA (US)

( * ) Notice: Subject to any disclaimer, the term of this patent is extended or adjusted under 35 U.S.C. 154(b) by 851 days.

(21) Appl. No.: 12/092,628

(22) PCT Filed: Oct. 26, 2006

(86) PCT No.: PCT/US2006/060271
§ 371 (c)(1),
(2), (4) Date: Feb. 8, 2011

(87) PCT Pub. No.: WO2007/053810
PCT Pub. Date: May 10, 2007

(65) Prior Publication Data
US 2011/0129523 A1 Jun. 2, 2011

Related U.S. Application Data

(63) Continuation-in-part of application No. 11/230,277, filed on Sep. 20, 2005, and a continuation-in-part of application No. 11/163,979, filed on Nov. 6, 2005, now Pat. No. 8,349,359.

(60) Provisional application No. 60/863,015, filed on Oct. 26, 2006, provisional application No. 60/522,785, filed on Nov. 7, 2004.

(51) Int. Cl.
*A61K 9/127* (2006.01)

(52) U.S. Cl.
USPC .......................................................... 424/450

(58) Field of Classification Search
USPC .......................................................... 424/450
See application file for complete search history.

(56) References Cited

U.S. PATENT DOCUMENTS

| | | |
|---|---|---|
| 6,429,219 B1 | 8/2002 | Pearson et al. |
| 6,660,756 B2 | 12/2003 | Challenger et al. |
| 6,764,693 B1 * | 7/2004 | Smith .......................... 424/450 |
| 2001/0053356 A1 | 12/2001 | Mousa |
| 2002/0025313 A1 | 2/2002 | Micklus |
| 2002/0136763 A1 | 9/2002 | Demopoulos et al. |
| 2003/0059462 A1 | 3/2003 | Barenholz |
| 2004/0071770 A1 * | 4/2004 | Smith .......................... 424/450 |
| 2004/0170560 A1 | 9/2004 | Fossheim |
| 2005/0100619 A1 | 5/2005 | Chen et al. |
| 2006/0171935 A1 | 8/2006 | Abeliovich |

OTHER PUBLICATIONS

Suntres, Z.e., et al J. Pharm. Pharmacol. vol. 46, pp. 23-28, 1994.*
Wendel, A. et al Biochemical Pharmacology, vol. 31, No. 22, pp. 3607-3611, 1981.*
Junghans, A., et al Free Rad. Res. vol. 33, pp. 8010808, 2000.*
Jellinger, KA, The role of iron in neurodegeneration: prospects for pharmacotherapy of Parkinson's disease, Drugs Aging Feb. 1999: 14(2): 115-40 (Adis Internatonal Limited 1999) PMID 10084365.
Sechi G et al, Reduced intravenous glutathione in the treatment of early Parkinson's disease, Prog. Neuropsychopharmacol Biol. Psychiatry, Oct. 1996; vol. 20(7): 1159-1170 Elsevier Science, Inc. 1996) PMID 8938817.
Bharath, S et al, Glutathione, iron and Parkinson's disease, Biochem Pharmacol. Sep. 2002;64(5-6):1037-48, (Elsevier Science, Inc. 2002) PMID 12213603.
Wendel A. et al,Drug-induced lipid peroxidation in mice-III. Glutathione content of liver, kidney and spleen after intravenous administration of free and liposomally entrapped glutathione, Biochem Pharmacol. Nov. 15, 1982; vol. 31 (22):3607-11 (Pergamon Press, Ltd. 1982) PMID 7181941.
Junghans A et al, Carotenoid-containing unilamellar liposomes loaded with glutathione: a model to study hydrophobic-hydrophilic antioxidant interaction, Free Radical Research, Dec. 2000;33(6):801-8. (Overseas Publishers Association N.V. 2000) PMID 11237102.

* cited by examiner

*Primary Examiner* — Gollamudi Kishore
(74) *Attorney, Agent, or Firm* — Brooke Schumm, III; Daneker, McIntire, Schumm, Prince, Manning & Widmann P.C.

(57) ABSTRACT

The invention proposes the sure of reduced glutathione in a liposome (liposomal reduced glutathione) for the oral administration of a therapeutically effective amount to ameliorate the progression of vascular disease, including atherosclerosis, diabetes, hypertension, narrowing of arteries leading to decreased blood flow, ischemic events, and the formation of blood clots, abnormal platelet aggregation, and thrombotic events, by reducing the amount and effect of oxidized cholesterol, oxidized HDL and oxidized LDL. The invention also proposes combining liposomal encapsulated glutathione with statin drugs to improve the effect of lowering not only cholesterol but also the oxidized cholesterol as well as oxidized HDL and oxidized LDL. The invention also proposes combining liposomal encapsulated glutathione with CoQ10 as a therapy for vascular disease and management of side effects of statin therapy.

Figure 1:
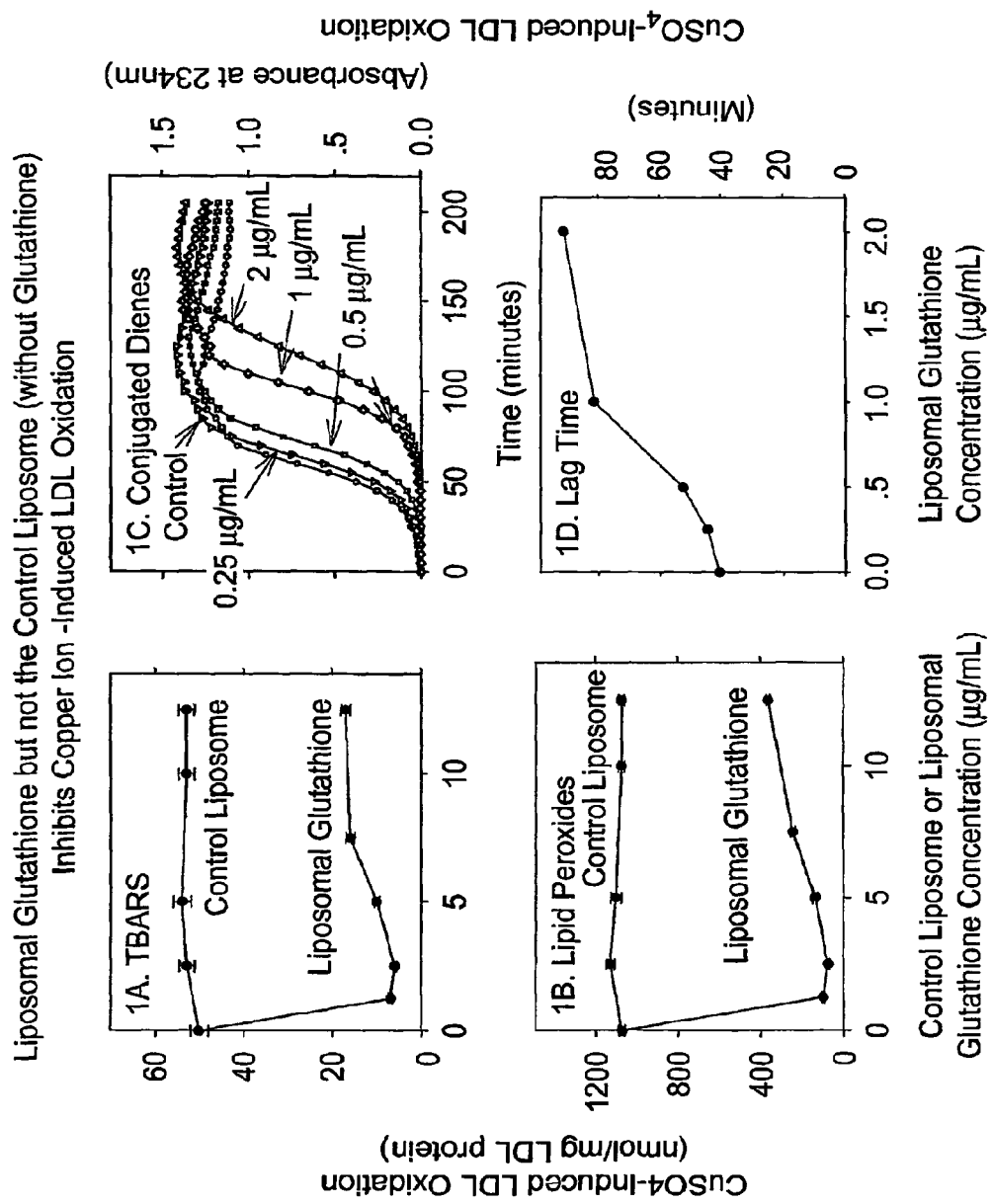

1 Claim, 5 Drawing Sheets under certain circumstances of stress such as damage to endothelial cells can undergo oxidative changes and be the inciting and continuing process by which atherosclerosis occurs.

LIPOSOMALLY ENCAPSULATED REDUCED GLUTATHIONE, INCLUDING WITH OTHER PHARMACOLOGIC PREPARATION, CAPABLE OF ADMINISTRATION AS AN ORAL, TOPICAL, INTRAORAL OR TRANSMUCOSAL, PREPARTION, FOR REVERSAL AND PREVENTION OF OXIDATION OF CHOLESTEROL AND OF LOW DENSITY LIPOPROTEIN

CONTINUATION DATA

This application is a section 371 entry into the U.S. National stage of PCT/US06/60271 filed Oct. 26, 2006 which claimed benefit and/or priority from U.S. Provisional application 60/863,015, and for purposes of the United States, this is a continuation in part of U.S. Utility patent application Ser. No. 11/230,277 filed on Sep. 20, 2005 with the title of "Combination and method using EDTA combined with glutathione in the reduced state encapsulated in a liposome to facilitate the method of delivery of the combination as an oral, topical, intra-oral or transmucosal for anti-thrombin effect and for anti-platelet aggregation and measurement of efficacy," and a continuation-in-part of U.S. utility application Ser. No. 11/163,979 filed Nov. 6, 2005, now patented as U.S. Pat. No. 8,349,359, which claimed benefit of U.S. Provisional Appl. 60/522,785 filed Nov. 7, 2004.

FIELD OF INVENTION

The invention proposes the use of glutathione in the reduced state encapsulated in a liposome alone or in combination with cholesterol lowering pharmacologic preparations such as statins for treatment of vascular deficiency diseases related to the formation of oxidized cholesterol, and/or oxidation and formation of low density lipoprotein (LDL) and of high density lipoprotein (HDL) that contribute to the formation of vascular disease states such as atherosclerosis and diabetes.

SUMMARY OF INVENTION

The invention is the method of management of disease related to oxidation of cholesterol, low density lipoprotein and high density lipoprotein using an orally available liposomal encapsulation of reduced glutathione alone or in combination with pharmacologic agents and the underlying combination of liposomal encapsulation of reduced glutathione and such agents. The invention uses the novel finding that the glutathione peroxidase enzyme naturally accompanies these native lipoproteins, particularly HDL and LDL cholesterol, to prevent the oxidative changes that are central mechanisms in the formation of atherosclerosis and vascular disease. However, such glutathione peroxidase requires either liposomal glutathione alone or in combination with existing pharmaceutical agents to prevent, to potentially reverse, and to improve symptoms of disease states related to the oxidation of lipids such as cholesterol, high density lipoprotein and low density lipoprotein. This invention, enables the prevention of oxidation of both HDL and LDL. Compounds enhancing the effect of the liposomal glutathione are contemplated such as selenium, and HMG-CoA reductase inhibitors. Reference will be made to atherosclerosis, but that reference is not meant to be limiting, but rather to be illustrative and the invention as it applies to atherosclerosis is applicable to vascular disease generally, and vascular associated difficulties such as erectile dysfunction. Vascular disease, for purposes of specification of the invention, is intended to include vascular disease generally; and to specifically include atherosclerosis, diabetes, hypertension, narrowing of arteries leading to decreased blood flow, ischemic events, and the formation of blood clots, abnormal platelet aggregation, and thrombotic events.

BACKGROUND

In order to examine the problems presented by the background which follows, one inventor inaugurated a study as yet unpublished called: "The effect of liposomal glutathione on the oxidation of the cholesterol components known as Low density lipoprotein (LDL) and high density lipoprotein (HDL)." Observations with respect to the interaction between glutathione peroxidase, liposomal reduced glutathione, and HDL and LDL led to this invention. In particular, the study highlighted the importance of reduced glutathione in maintaining the normal state of function of HDL and LDL, apparently by lowering the oxidation state of LDL and HDL. Other antioxidants may provide indirect support for normal function, but reduced glutathione functions much more efficiently and effectively. Further, it was determined that synergistic effect could be achieved by potentially using lower doses of statins than are usually required, reducing side effects while sustaining the intended function of the statin. Moreover, the addition of CoQ10 or ubiquinone could ameliorate one of the side effects of statins.

It was estimated in 2001 that 60 million Americans had heart disease (Lefkowitz). This number translates to a statistic that more than 1 out of every 5 individuals has heart disease. While an array of interventions, both medical and surgical have reduced the death rates in the decade ending 1997 by 20%, 12.2 million Americans have a history of heart attack, chest pain or both. With 1 million in the US dying of cardiovascular disease each year, it remains that nation's leading cause of death.

Concepts of related to the development of atherosclerosis are evolving. Elevations of the fatty material in blood such as cholesterol have been associated with increased risk of coronary artery disease (Castelli). However, more than half of the individuals with coronary artery disease have total levels of cholesterol that are less than the level considered normal, that is <200 mg/dL (Lavie). Thus, additions to the current methods of management of atherosclerosis are needed to change the prevalence of this disease.

Three theories of the cause of atherosclerosis have emerged recently in regard to the cause of atherosclerosis. Their emphasis is overlapping in terms of the events necessary to support the development of atherosclerosis (Stocker) and is reviewed in detail in Stocker's article (Stocker R, Keaney J F Jr. Role of Oxidative Modifications in Atherosclerosis. Physiological Review, Oct. 1, 2004; 84(4): 1381-1478. PMID: 15383655 http://physrev.physiology.org/cgi/content/full/84/4/1381).

These theories in include:
  Response to injury: This refers to damage to the arterial lining cells called endothelial lining cells by various factors such as shear stress, infection and inflammation, and even the mechanical trauma of interventions such as arterial stent placement.
  Response to retention: This refers to the concept that fatty materials such as lipoprotein retention is the inciting event for atherosclerosis. The emphasis is on the retention of a particular lipoprotein called Low Density Lipoprotein (LDL).
  Oxidative modification: This hypothesis focuses on the concept that LDL in its native, that is non-oxidized state, is not atherogenic. However, LDL modified by chemical reactions results in the oxidized form of LDL or oxidized LDL (ox LDL). OxLDL is readily internalized by macrophages and can lead to the formation of foam cells and the sequence of events associated with the formation of atherosclerosis.

Oxidative modification can also be triggered by exposure of vascular cells to transition metals, which results in the oxidation modification of cholesterol, HDL and LDL. The concept that transition metals can trigger oxidation of LDL has been reviewed in the U.S. patent application Ser. No. 11/230,277 by Guilford, entitled "Combination and method using EDTA combined with glutathione in the reduced state encapsulated in a liposome to facilitate the method of delivery of the combination as an oral, topical, intra-oral or transmucosal for anti-thrombin effect and for anti-platelet aggregation and measurement of efficacy".

The tripeptide L-glutathione (GSH) (gamma-glutamyl-cysteinyl-glycine) is well known in biological and medical studies to serve several essential functions in the cells of higher organisms such as mammals. It is functional when it appears in the biochemical form known as the reduced state (GSH). When oxidized, it forms into a form known as a dimer (GSSG).

Glutathione in the reduced state (GSH) in this invention functions as the specific substrate for the enzyme glutathione peroxidase, which enzyme functions to inhibit cholesterol, particularly HDL and LDL oxidation. The enzyme cooperates with the GSH to maintain the HDL and LDL in a reduced and functional state. Antioxidants such as Vitamin C or vitamin E will not cause that functionality. GSH also functions as an antioxidant, protecting cells against free-radical mediated damage, acting as a detoxifying agent by transporting toxins out of cells and out of the liver, and acting as or facilitating cell signals, particularly in the immune system. GSH is particularly active with respect to 2OH$^-$ radicals, because 2 GSH$^-$ each easily substitute their S—H bonds. Upon such substitution, the two "GS-molecules" bond to each other into an oxidized state forming GSSG, and the 2OH$^-$ radicals are reduced in charge and in number of free electrons by each hydroxyl radical bonding with an H atom from the thiol group of GSH. Most glutathione taken orally and even NAC taken orally are not presented in an intracellular context as reduced glutathione. There was and is a need for reduced glutathione and a means of transport of reduced glutathione. Further, the substance to address HDL and LDL oxidation must be able to interact with glutathione peroxidase that is on the surface of the cell.

A deficiency of glutathione (reduced) may lead to damage to cells and tissues through several mechanisms including the accumulation of an excess of free radicals which causes disruption of molecules, especially lipids causing lipid peroxidation, and which, combined with toxin accumulation, will lead to cell death. As a general term, these mechanisms are often referred to as oxidation or peroxidation. The lack of sufficient glutathione in the reduced state relative to the oxidized state may be due to lack of production of glutathione (reduced) or an excess of the materials such as toxins that consume glutathione (reduced). The lack of glutathione (reduced) may manifest as a systemic deficiency or locally in specific cells undergoing oxidation stress.

Hastings et al, U.S. Pat. No. 6,368,617 reference the combination of glutathione and CoQ10 in combination with 7-keto dehydroepiandosterone (7-keto DHEA) for a health promoting combination. There is no reference for the use of this combining of liposomal encapsulation of reduced glutathione combined with CoQ10 for prevention or treatment of oxidized cholesterol and its vascular effects.

Richardson et al U.S. Pat. No. 6,207,190 reference the use of an oral combination of at least 4 materials including folic acid, magnesium, lipoic acid and N-acetyl-cysteine which is used as a source of glutathione for the treatment of glaucoma, a disease of the eye. While their patent references the use of glutathione to stabilize Nitric Oxide (NO), there is no reference to its use systemically to limit damage to endothelial lining cells of arteries or prevent the oxidation of cholesterol, HDL and LDL or the deleterious sequence of events that occur related to these oxidation products, nor any reference to reduced glutathione.

A review of the literature reveals one study of the effect of the intravenous infusion of reduced l-glutathione (Intravenous refers to the method of administration of aqueous materials using an infusing tube inserted through a vein to facilitate direct venous system administration.) The study using the intravenous infusion of reduced glutathione given in a dose of 600 mg twice a day for a week suggested that there may be clinical benefit to the infusion of glutathione (Arosio). There is no reference to the use of an orally absorbable form of glutathione in the article and no reference to the use of liposomal glutathione. The article also has no reference to the reduction of oxidized lipids.

Rodriguez et al, in U.S. Pat. No. 6,773,719 reference the use of plain liposomes in the management of atherosclerosis. The mechanism involves the removal of the excess lipids by the liposomes. There is no reference to using reduced glutathione in the liposomes, and no reference as to how to enable liposomal reduced glutathione to cooperate effectively with GpOx. The mechanism of this invention is not direct to removal of excess lipids.

Williams, U.S. Pat. No. 6,367,479 references the use of large unilaminar liposome that is single walled, vesicles like liposomes for the transport of cholesterol from arterial vessels back to the liver. However, there is no reference to liposomes containing reduced glutathione or to the use of liposomes containing reduced glutathione for the management of disease related to oxidation of lipids such as cholesterol, HDL or LDL.

Demopoulos et al in U.S. Pat. No. 6,350,467 references the use of a pharmaceutical preparation of a combination that includes glutathione in a powdered form for the treatment of atherosclerosis. However there is no reference for the use of the preparation for management of oxidized lipids such as cholesterol, HDL or LDL. There is also no mention of the use of the preparation in a liposome nor the use of reduced glutathione in a liposome.

Smith, U.S. Pat. No. 6,764,693 references the use of liposomes containing a combination of glutathione in combination with at least one other antioxidant material to increase intracellular and extra cellular antioxidants. There is no reference to liposomes containing reduced glutathione which is what is needed to cooperate with glutathione peroxidase in order to prevent oxidation of HDL and LDL, nor is there any reference to the use of liposomes containing reduced glutathione for the management of disease related to oxidation of lipids such as cholesterol, HDL or LDL.

Meyerhoff, U.S. Pat. No. 6,469,049, Oct. 22, 2002, references the combination of lipoic acid and glutathione or CoQ10 for the management of central nervous system injuries, but does not reference the use of glutathione and CoQ10 together nor in the management of vascular disease. Likewise, there is no reference to the combination of glutathione, CoQ10 and statins, nor reduced glutathione, CoQ10 and statins, nor liposomal encapsulation of reduced glutathione, CoQ10 and statin for the management of atherosclerosis or elevated cholesterol or oxidized cholesterol or oxidized LDL or HDL.

Cooke in US patent application 20020151592 references the use of arginine or lysine to increase nitric oxide production for vasodilation purposes and he also references the use of glutathione as an antioxidant used in conjunction with arginine. However, there is no mention of the use of reduced glutathione, nor is there mention of the use of liposomal encapsulation of glutathione or reduced glutathione to supply the reduced glutathione needed for maintaining adequate GSNO formation. The current invention is also distinguished from the reference by Cooke in that the current invention supplies reduced glutathione in a form that is readily absorbable into the body, where plain powdered glutathione is not well absorbed as reviewed in the previously referenced application, Guilford U.S. application Ser. No. 11/163,979 filed Nov. 6, 2005.

Oxidative stress occurs when there is an imbalance between free radical production and antioxidant capacity (Penckofer). This may be due to increased free radical formation in the body and/or loss of normal antioxidant defenses. Oxidative stress is defined as excessive production of reactive oxygen species (ROS) in the presence of diminished antioxidant substances (Opara).

Reactive oxygen species (ROS) are generated as by-products of normal cellular metabolism, primarily in the mitochondria (Miyamoto), or as a result of external biochemical stress or in response to inflammatory stimuli. When the cellular production of ROS exceeds the cell's antioxidant capacity, cellular macromolecules such as lipids, proteins and DNA can be damaged. Damage to these biochemicals leads to the concept of 'oxidative stress', which is thought to contribute to aging and pathogenesis of a variety of human diseases. The body's defense against oxidative stress is accomplished by interconnecting systems of antioxidant micronutrients (vitamins and minerals) and enzymes. While the vitamins act as donors and acceptors of ROS, minerals regulate activity of the enzymes (Opara).

A combination of factors cause atherosclerosis. The imbalance between circulation levels of cholesterol transported in HDL versus LDS is intimately associated with dysfunction in the lining of arteries and oxidation stress in the arterial wall cells. This dysfunction is closely related to inflammation. Dyslipidemia, oxidation stress and inflammation are closely interrelated to the development of atherosclerosis. OxLDL leads to a series of inflammatory events related to immune modulator release from macrophages that ingest the oxidized lipid. It has been demonstrated that most of the proinflammatory properties of oxLDL result from products of the oxidation of LDL. This perspective gives the view that atherosclerosis is a chronic inflammatory disease of the arterial wall mediated by oxLDL in concert with a range of proinflammatory agents (Kontush). Based on the unpublished study by Aviram, discussed herein, called "The effect of liposomal glutathione on the oxidation of the cholesterol components known as Low density lipoprotein (LDL) and high density lipoprotein (HDL)," lack of available reduced glutathione to maintain normal antioxidant function in LDL and lack of reduced glutathione to maintain the normal antioxidant function of HDL appears to be intimately related to maintenance of normal artery function and development of atherosclerosis. The absence of adequate glutathione is the common factor resulting from dyslipidemia, and leads to oxidation stress. Thus adequate biochemically reduced glutathione mediates the inflammation associated with atherosclerosis.

The present invention, liposomal reduced glutathione, offers a novel method to maintain cholesterol, LDL and HDL in their reduced, functional state, which will delay or avoid the progression of events leading to atherosclerosis. The current invention offers a method of oral administration of an absorbable material that is needed to supply the physiologic substrate needed to work with glutathione peroxidase in the maintenance of normal artery lining cell function and potentially slow, stop or reverse vascular disease by deterring creation of Oxidized LDL or HDL.

Oxidation stress is related to many disease states. Depending on the gradation of the stress effect a diverse array of disease states are related to oxidation stress. These diseases include cardiovascular diseases, neurological diseases, malignancies, renal diseases, diabetes, inflammatory problems, skin diseases, aging, respiratory diseases, liver diseases and different types of viral infections (Irshad).

Normal metabolism forms free radicals, leading to oxidation. These metabolites either from oxygen or nitrogen are called pro-oxidants. The stress component refers to changes that put higher demands on the available antioxidants. The demand for increased antioxidants may pull energy away from the production of other cell metabolites and/or slow their formation. When the state of oxidation increases it can begin to interfere with cell function. With oxidation stress the changes could still be reversible, even if only reversible in part, with the addition of the appropriate antioxidant.

As the cell changes and oxidation damage occurs, the change and damage become less reversible and begin to increase to include macromolecules in the cells including protein, DNA and the lipids found in membranes. The result is initially seen as cell damage and when widespread can be seen as tissue damage.

To counterbalance the deleterious effects of oxidation stress, the body uses an array of nutrients and metabolites called antioxidants. Antioxidants are provided by the normal metabolism of the body or from outside sources such as vitamin C. Antioxidants include superoxide dismutase, catalase, glutathione peroxidase and glutathione reductase, as well as minerals like Se, Mn, Cu and Zn, and vitamins like vitamin A, C and E. Other compounds with antioxidant activity include glutathione, flavonoids, bilirubin and uric acid (Irshad). Selenium is contemplated as part of the preferred composition of the invention as selenium has been shown to increase the availability of glutathione peroxidase in the serum of individuals under oxidative stress and who had been observed to have low glutathione system function (Hussein).

There is a growing awareness that the glutathione related antioxidant system plays a key role in the prevention of oxidation stress. For example, in patients with coronary artery disease, a below-normal level of the glutathione related enzyme called glutathione peroxidase-1 has been found to be independently associated with an increase risk of cardiovascular events (Blankenberg). Glutathione plays such a crucial role in management of oxidation stress that deficiency of glutathione is now being referred to as part of the definition of oxidation stress. Some articles use the general definition that describes the situation in the following manner, "Oxidative stress has been defined as a loss of counterbalance between free radical or reactive oxygen species (ROS) production and antioxidant systems." (Dursun). More recently, many authors are defining oxidation stress as dependent on the availability and function of the glutathione system, as exemplified by the statement from a recent article, "Oxidative stress may be viewed as an imbalance between reactive oxygen species (ROS) and oxidant production and the state of glutathione redox buffer and antioxidant defense system" (Tappia).

Another example is the description of oxidation stress found in diabetes, "Patients affected by diabetes mellitus have oxidative stress with an impaired glutathione (GSH) redox state." (Bravi)

In spite of the awareness of the role of oxidation stress in disease there is a persisting controversy in regard to the role of oxidation stress in the development of atherosclerosis. While there is adequate research demonstrating the role of oxidation stress related to atherosclerosis, antioxidants such as vitamin E or beta-carotene (Clarke) or vitamins A, C, and E, and beta carotene (Hasnain) have not been effective in and of themselves in reducing cardiovascular death and morbidity in human clinical trials. This has led many investigators to question the importance of oxidation stress in human atherosclerosis (Madamanchi). It is proposed in this application that the failure to observe benefit of antioxidant therapy in atherosclerosis may be due to the lack of the appropriate antioxidant for the situation.

Much of the confusion regarding the role of glutathione in management of vascular disease may be related to two concepts. The first is that it has been previously thought that glutathione peroxidase is not found outside the cell or in extracellular fluids (Stocker). The second concept is that human clinical studies with antioxidants in vascular disease in general have been disappointing (Cynshi). However, there have been no prior studies of the use of an oral preparation of glutathione in its reduced form or the use of liposomal encapsulation of reduced glutathione for the prevention of atherosclerosis.

A human study observing the relationship between oxidation status and thickening of the lining of the carotid artery, measured by ultrasound has established a relationship with the level of available reduced glutathione (Ashfaq). Carotid artery intimal thickening has been shown to correlate with both risk factors of atherosclerosis and the presence of coronary artery atherosclerosis (Crouse). The factors correlated with increased carotid artery intimal thickening were the absolute level of reduced glutathione and the ratio of reduced glutathione (gsh) and oxidized glutathione (gssg). In the Ashfaq study, the single variable that most closely predicted increased intimal thickening was the ratio of reduced glutathione to oxidized glutathione or gsh/gssg. The more reduced glutathione relative to oxidized glutathione that was available, the less intimal thickening was observed.

Low Density Lipoproteins commonly known as LDL refers to a class of lipoprotein particles. The lipid component is composed of the fatty acid molecules associated with cholesterol. The protein component consists of apoprotein B-100 and Apo E. LDL particles are identified by their size (18-25 nm diameter) and their components. Apolipoproteins of the B category are found in LDL and Apoprotein B-100 is the key protein associated with LDL. This protein is retained within the artery wall in close association with the proteoglycans found in the artery wall and play an important role in the formation of atherosclerosis. Therefore, the term LDL will refer to "native" apolipoprotein B-100, and oxLDL will refer to oxidized apoprotein B-100. Further, these terms will refer to the additional proteoglycans associated with the sites of atherosclerotic lesions and lipoprotein deposition.

High Density Lipoprotein (HDL) is a smaller molecule (8-11 nm diameter). These particles function to carry cholesterol from tissues that do not need cholesterol back to the liver. This is a key function of HDL related to the preventing the accumulation of too much LDL in the cells lining arteries. As the HDL particles have the potential to remove cholesterol from plaque in the arteries it is also known as "good cholesterol". The density of HDL derives from its small size and the high proportion of protein that they contain. These lipoproteins play a role in gathering the cholesterol. For example, HDL contains an apolipoprotein (apo) called A-I. ApoA-I is the major protein component of antiatherogenic high-density lipoprotein (HDL). As the HDL circulates it may increase in size as it incorporates more molecules of cholesterol into its structure. One of the methods of antioxidant function of HDL is through its ability to bind transition metal ions such as iron and copper, which are potent catalyzers of LDL oxidation (Kunitake). A low level of HDL is statistically correlated as a risk factor for coronary artery disease (Kontush). Even in individuals on cholesterol lowering therapy, the level of HDL remains a significant predictor of cardiovascular events. Thus, the ability of HDL to function in its native or biochemically reduced state is critical to the normal function and the avoidance of atherosclerosis. Oxidation of HDL impairs the ability of HDL to promote cholesterol efflux by the ATP-binding cassette transporter A-1 pathway (Navab). HDL can become oxidized through oxidation stress, diabetes and exposure to free radicals generated from transition metals and oxHDL does not function as efficiently as the native HDL. Thus, there is increasing attention focused not only on the quantity of HDL, but also the oxidation state of HDL.

The term oxidation stress is used to define the metabolic events associated with damage from free radicals related to stress in cells and organ tissues. The concepts behind thus descriptive are familiar to persons reasonably skilled in the art; yet defining these events remains difficult. No literature or prior art has suggested how to manage that oxidation state of HDL nor has any prior art or literature suggested using glutathione reduced or an oral liposomal encapsulation of reduced glutathione to alter the oxidation state of HDL.

HDL has become recognized as playing a key role in both removing excess LDL and maintaining LDL in the non-oxidized state. Thus, methods that maintain normal function of HDL play a vital role in maintaining both normal LDL levels, as well as preventing the oxidation of LDL. The combined effect of the present invention liposomal glutathione in maintaining normal reductive efficacy of glutathione peroxidase (GPx) associated with cholesterol, LDL and HDL as well as its action on Phospholipid Hydroperoxide Glutathione Peroxidase (PH-GPx), an antioxidant enzyme that is able to directly reduce lipid peroxides even when they are bound to cellular membranes, creates the novel and surprising effect of decreasing lipid peroxidation by supplying the natural component, reduced glutathione, which the stress of excess toxins has diminished. Prior to the present invention, there has been no method of providing systemic availability of reduced glutathione to support these natural systems, and particularly to support both intracellular and cellular-membrane lipids and lipid derivatives. The surprising finding that glutathione peroxidase is present on LDL and HDL allows the present invention to provide a novel route for support cooperative effect that is normally present in the body to protect against damage from the formation of oxLDL. Thus, the present invention, liposomal glutathione (reduced) both prevents the oxidation of LDL, as well as maintaining HDL in a non-oxidized state so that its function is also maintained on both the cell membrane and in the cell. The present invention is a novel composition that is convenient, stable and orally available for maintaining normal levels of reduced glutathione even in conditions where the ability of the system to maintain natural glutathione levels has been overburdened or compromised. In situations such as an excess of oxidized LDL, excess cholesterol or other oxidizing stress situation, the current invention provides a convenient method of maintaining LDL in the non-oxidized state.

Figure 5:
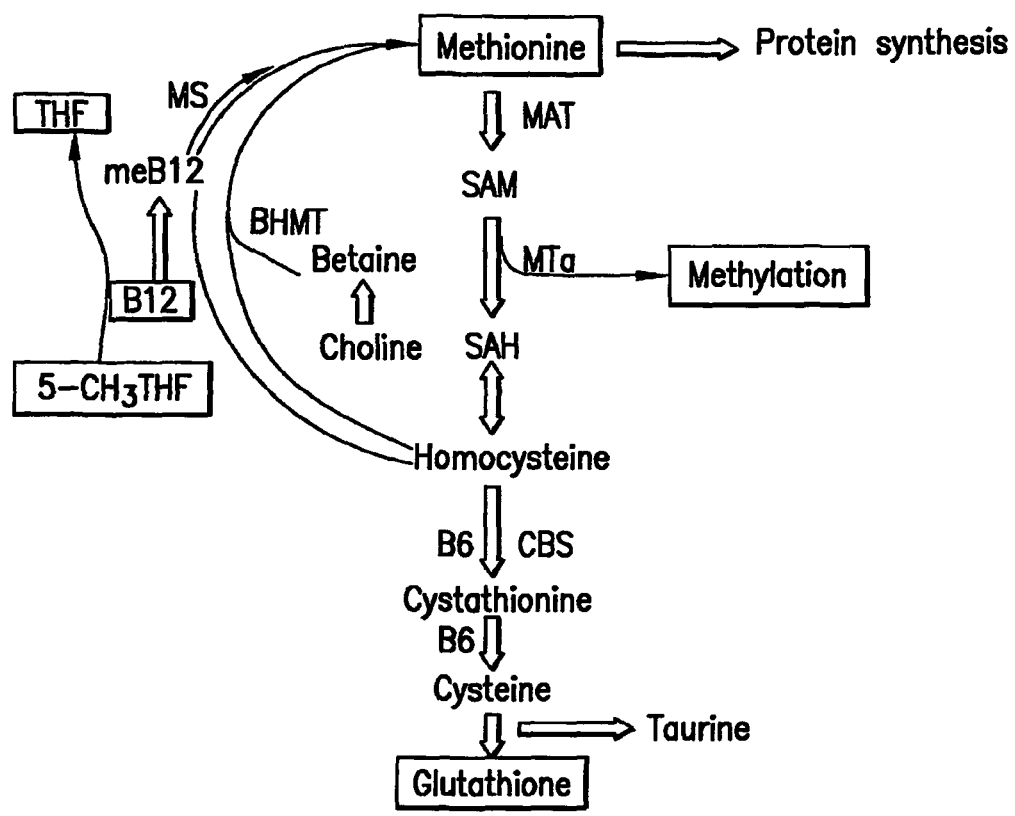

The use of a precursor of glutathione, N-acetyl-cysteine (NAC) has been referenced by Kindness, Guilford et al in US Patent application published as 20020182585, published Dec. 5, 2002, as a preferred mode of an invention using NAC to build glutathione. While it has been observed that cysteine is an amino acid component of the tripeptide glutathione, recent observations such as reviewed in Example 2, suggest that the direct delivery of reduced glutathione is more effective. It is known that cysteine can also be directed to form taurine. Taurine is one of the most abundant amino acids in the body and in certain situations the formation of glutathione can be altered in favor of the formation of taurine. Taurine does have antioxidant properties, but does not interact with the enzyme system that supports the glutathione antioxidant system, such as glutathione peroxidase. The preference for the production of taurine over glutathione is reported to occur with inflammation (Santangelo) and toxins such as alcohol (Jung) and in this application is reported to occur with in the presence of an excess burden of mercury in the human system. For the purpose of this discussion this switch in biochemical pathways will be referred to as the "taurine shunt", and is illustrated in FIG. 5. The abbreviations in FIG. 5 are as follows: THF: tetrahydrofolate; MS: methionine synthase; BHMT: betaine-homocysteine methyltransferase; MAT: methionine adenosyltransferase; SAM: S-adenosylmethionine; SAH: S-adenosylhomocysteine; SAHH: SAH hydrolase; ADA: adenosine deaminase; AK: adenosine kinase; CBS: cystathionine beta synthase; B12: cyanocobalomine; meB12: methylcobalamine; 5-CH$_3$ THF: 5-Methyltetrahydrofolate.

This finding of preference for the production of taurine over glutathione is significant as the shunt from glutathione production to taurine may occur locally in tissues and cells and may be a contributing factor to the local as well as systemic reduction of reduced glutathione found in atherosclerosis. In addition, an excess of taurine as evidenced by increased excretion of taurine in the urine has been observed by the applicant in children with autism, who are documented to have low levels of glutathione systemically.

The presence of the "taurine shunt" makes the liposomal encapsulation of reduced glutathione the preferred mode for the delivery and maintenance of reduced glutathione for the present invention.

The combination of an HMG-CoA reductase inhibitor and CoQ10 has been referenced by Brown in U.S. Pat. No. 4,933,165, Jun. 12, 1990. There is no reference to liposomes in Brown '165 nor to the use of reduced glutathione in combination with a statin, nor with a statin and CoQ10. The use of CoQ10 with a statin is distinctly different from the combination of liposomal glutathione and statin. The CoQ10 is added to replace the loss of CoQ10 that occurs with the use of the HMG-CoA reductase inhibitor. In the present invention embodiment, the unique concept is that the liposomal glutathione is added to enhance the effect of maintaining cholesterol and LDL in the biochemically reduced state. By maintaining the reduced state, that is avoiding the oxidation of Cholesterol or the oxidation of LDL, the most beneficial effect of reduced glutathione and a statin working together is achieved. Further, the goal of lessening the formation of atherosclerosis will be achieved using a lower dose of the statin drug and thereby minimizing the side effects of the statin. The current goal of treatment by a statin has been to lower the level of LDL to lessen the progression of atherosclerosis. The goal of the combination in the current invention is to lessen the progression of atherosclerosis by lessening the formation of oxLDL, and facilitating the function of HDL. As has been noted, decreased oxLDL is advantageous in avoiding atherosclerosis. There is no reference to the combination of HMG-CoA reductase inhibitor, CoQ10 and glutathione as related in the current invention.

The intravenous administration of reduced glutathione has been reported to have benefit in improving blood flow in peripheral vascular disease (Arosio), however there has been no reference to the mechanism of maintaining or returning lipid peroxidation to the reduced (non-oxidized) state using glutathione as a substrate for the glutathione peroxidase that has been found to be associated with native cholesterol, LDL and HDL as reported in this invention. The interaction of glutathione naturally with glutathione peroxidase associated with these lipids in the circulation represents a critical step in the prevention of atherosclerosis. The novel and surprising aspect of being able to supply reduced glutathione in an orally absorbable liposome creates an exciting new method for the study and management of atherosclerotic vascular disease that has not been previously reported. The ability to supply reduced glutathione orally in the present invention represents a novel method of management of oxidation of lipids such as cholesterol, LDL and HDL and represents a significant advantage in disease management.

There is evolving in the literature the knowledge that a significant number of cardiovascular events occur in individuals with normal levels of HDL and LDL (Navab). This observation has stimulated investigations for biomarkers with higher predictive value. Recent articles have proposed that the level of oxidized LDL has high correlation with progression of vascular disease. There have been no reports of plain glutathione being capable of absorption in the human to provide adequate levels of support for the glutathione system. The liposomal encapsulation of reduced glutathione provides a novel method for achieving effective systemic and intracellular delivery of glutathione (reduced).

The function of LDL in the system is to carry cholesterol and triglycerides away from cells and tissue that produce more than they use, such as the liver, to cells and tissues that take up cholesterol, such as arteries. The normal state of these lipids is the biochemically reduced form. When altered by oxidation, these lipoproteins are identified as oxidized LDL or oxLDL.

LDL is often referred to as "bad cholesterol" as it has a statistical association with cardiovascular disease. The inventors believe it is not the LDL that is bad, but where and what state of oxidation the LDL molecule is in that may be the more compromising component of LDL metabolism. In terms of triggering the artery wall changes found in atherosclerosis, oxidized LDL is becoming known as the trigger for atherosclerosis. OxLDL has been shown to be a strong and independent risk factor of vascular disease such as coronary heart disease even in apparently healthy individuals (Meisinger). Thus, the search for a trigger for developing atherosclerosis, is shifting focus from the management of the LDL to the question of how to manage the oxidation state of LDL. No literature or prior art has suggested how to directly manage the oxidation state of LDL nor has any prior art or literature suggested using glutathione reduced or an oral liposomal encapsulation of reduced glutathione to alter the oxidation state of LDL.

Reactive Oxygen Species ("ROS") exert some functions necessary for cell homeostasis maintenance, but loss of the balance between the anti- and pro-oxidant states results in pathology. ROS mediated lipid peroxides are of critical importance because they participate in chain reactions that amplify damage to biomolecules including membranes and DNA. DNA attack gives rise to mutations that may involve tumor suppressor genes or oncogenes, and this is an oncogenic mechanism (Cejas). OxLDL has been observed to increase cell proliferation (Zettler) and has been considered one stimulant for the proliferation of smooth muscle. While it has been observed that oxLDL induces an increased expression of both the promoters and inhibitors of the cell cycle. Activating inducers and inhibitors should allow for self regulation of cell growth. The generalized induction of both cell cycle inducers and inhibitors with cooperation among the cell cycle regulators is consistent with the slower, non-malignant cell growth typical of an atherosclerotic plaque. While balance between stimulation and inhibition occurs in other non-malignant situations such as the rapid cell proliferation seen in liver regeneration, malignant cell growth is typically characterized by high levels of the one or more of the cell cycle inducers and low or absent cell cycle inhibitors.

Contrary to the unregulated cell cycle proliferation in cancer, one difference between regulated cell cycle proliferation in normal or atherosclerotic cells and unregulated cell cycle proliferation in cancer cells and in atherosclerotic cells is that the there is both an increase in expression and nuclear translocation of both the activators and inhibitors of the cell cycle. It is conceivable that the continued exposure of cell nuclei to excessive oxLDL could result in abnormal modulation of cell cycle reproduction, which in cancer means little or no modulation of reproduction.

Oxidation stress indicators have been found in various cancer cells and it is postulated that the redox imbalance may be related to stimulation of changes not only in the affected cells, but also in the body response toward cancer. Oxidative DNA abnormalities are noted in many tumors and it appears that oxidative DNA damage is linked with the process of initiation of cancer. As a variety of transition metals such as iron, copper, cadmium, arsenic and nickel are involved in the formation of the free radicals via reactions such as the Fenton reaction, a deficiency of reduced glutathione and the corresponding ability to modulate free radical formation may play a critical role in the induction of cancers. Thus, methods that maintain normal levels of metals such as iron and copper and remove the abnormal metals will be of significant benefit in avoiding the oxidative stimulation that can lead not only to atherosclerosis, but also to cancers. The use of liposomal glutathione and EDTA has been previously reviewed by Guilford, U.S. patent application Ser. No. 11/230,277 filed Sep. 20, 2005.

Additional impact from metals is observed with metals such as mercury, cadmium, nickel and arsenic, each of which also depletes glutathione (Valko, 2005). It is probable that metal induced oxidation stress may create an oxidative environment favorable to the development of cancer (Valko, 2006).

Patients with cancer have an increased amount of oxidation stress related to the disease process. The addition of chemotherapy agents increases the oxidation stress and risk of side effects such as neuropathy. For example, the occurrence of neuropathy has been found to limit the number of treatments with cisplatin. The use of intravenous reduced glutathione concurrent with the administration of cisplatin has been observed to allow increased dose intensity of treatments and to not interfere with the efficacy of the drug (Di Re). No prior art suggests the novel use proposed herein of the use of an oral liposomal preparation of reduced glutathione as described in this application for the reduction of side effects during chemotherapy. In addition, there are no reports of orally effective liposomal glutathione being used post chemotherapy to help restore normal glutathione levels.

Example 3 illustrates the effect that extensive disease related to cancer can have on the patient and the impact that the current invention may have on the treatment of an individual with cancer that can occur by the administration of the invention, liposomal glutathione. Cancer has been shown to be associated with an increase in oxidation stress in general particularly oxidized LDL. It is proposed that the current invention be considered as a component of cancer therapy, especially after therapies or at a stage of progression in which oxidation stress may have become overwhelming. While the dramatic improvement experienced by the individual was not permanent, it does demonstrate that the use of the current invention has relevance to the clinical management of cancer.

Oxidation stress creates a series of concurrent events, which affect the status of the cells lining arteries. While the oxidation stress effects on lipids are occurring another effect is the decrease in availability of nitric oxide produced by the endothelial cells.

Nitric oxide has the capacity to cause vasodilation, but if not stabilized, can also contribute the formation of free radicals called Reactive nitrogen species, which will actually contribute further to the cascade of oxidation locally in an artery. Nitric oxide has been shown to react with glutathione, which creates S-nitrosoglutathione (GSNO). The GSNO molecule is more stable than NO and has been demonstrated dilating effects directly in the lung, where it has been shown to dilator activity (Que). This mechanism is reviewed in Guilford, U.S. Application 60/596,171 filed 6 Sep. 2005 entitled "Method for the Treatment of Infection with HHV-6 Virus and the Amelioration of Symptoms Related to Virus Using Liposomal Encapsulation for Delivery of Reduced Glutathione and PCT/US2006/34648 filed 6 Sep. 2006.

In artery disease the presence of oxidized LDL creates an increased demand on the availability of reduced glutathione, leaving less glutathione available to create the GSNO molecule needed to stabilize nitric oxide (NO). Normally, the expansion of the artery prevents the increase in pressure that accompanies the contraction of the heart muscle pumping blood through the artery system. Without this vasodilatation capacity, an increase in the pressure in the artery will occur as the artery acts like a solid pipe. This increased pressure within the pipe-like artery is what we call hypertension. The lack of vasodilating action by GSNO leads to decreased relaxation in the artery and manifests as increased blood pressure, known has hypertension. An additional mode of action of the present invention is the introduction of reduced glutathione via the liposomes to provide the glutathione necessary for the creation of GSNO at sites of nitric oxide production and glutathione deficiency. This will be particularly beneficial in individuals with either elevations of oxidized LDL or increased LDL, which leads to increased oxLDL.

The ability to increase the efficacy of the natural mechanism of the blood pressure maintenance or to naturally facilitate the function of medications or supplements designed to maintain normal blood pressure is a novel and unexpected finding related to the use of liposomal glutathione. As reviewed in examples 4 and 5, the liposomal glutathione is effective in combination with either a nutrient that increases nitric oxide such as arginine or lysine or in combination with a prescription medication such as lisinopril in combination with arginine and the liposomal glutathione.

The preferred dose of the combination of the invention, liposomal glutathione, and arginine is liposomal glutathione 800 mg in combination with each 450 mg capsule of arginine. This combination may be taken once or twice a day as needed to maintain a normal blood pressure.

The preferred combination of the invention in combination with blood pressure medication is with lisinopril 20 mg daily, in combination with 800 mg of liposomal glutathione. This may be combined with arginine 450 mg as needed.

Additionally, in the situation where there is oxidized LDL being formed in the system an excess of reduced glutathione may need to be supplied in addition to the nitric oxide enhancing agent to maintain adequate formation of GSNO. The formation of GSNO is the normal reaction that occurs in the body to maintain the vasodilating properties of NO and requires a continuous supply of reduced glutathione to be formed. An excess of oxidation stress will create the situation where the body needs to supply an excess of reduced glutathione via the current invention, liposomal glutathione, to be able to utilize the nitric oxide that is formed.

The management of elevated blood pressure uses medications that fall into the following categories:

1. Diuretics
   chlorthalidone (Hygroton), furosemide (Lasix), hydrochlorothiazide (Esidrix, Hydrodiuril, Microzide), indapamide (Lozol), metolazone (Mykrox, Zaroxolyn)
2. Potassium-sparing diuretics
   amiloride hydrochloride (Midamar), spironolactone (Aldactone), triamterene (Dyrenium)
3. Combination diuretics
   amiloride hydrochloride+hydrochlorothiazide (Moduretic), spironolactone+hydrochlorothiazide (Aldactazide), triamterene+hydrochlorothiazide (Dyazide, Maxzide)
4. Beta-blockers
   acebutolol (Sectral), atenolol (Tenormin), betaxolol (Kerlone), bisoprolol fumarate (Zebeta), carteolol hydrochloride (Cartrol), metoprolol tartrate (Lopressor), metoprolol succinate (Toprol-XL), nadolol (Corgard), penbutolol sulfate (Levatol), pindolol (Visken), propranolol hydrochloride (Inderal), timolol maleate (Blocadren).
5. Angiotensin Converting Enzyme Inhibitors (ACE inhibitors)
   benazepril hydrochloride (Lotensin), captopril (Capoten), enalapril maleate (Vasotec), fosinopril sodium (Monopril), lisinopril (Prinivel, Zestril), moexipril (Univasc) quinapril hydrochloride (Accupril), ramipril (Altace), trandolapril Mavik.
6. Angiotensin II receptor blockers
   candesartan (Atacand), irbesarten (Avapro), losartin potassium (Cozaar), valsartan Diovan
7. Calcium channel blockers
   amlodipine besylate (Norvasc), diltiazem hydrochloride (Cardizem CD, Cardizem SR, Dilacor XR, Tiazac), felodipine (Plendil), isradipine (DynaCirc, DynaCirc CR), nicardipine (Cardene SR), nifedipine (Adalat CC, Procardia XL), nisoldipine (Sular), verapamil hydrochloride (Calan SR, Covera HS, Isoptin SR, Verelan).
8. Alpha blockers
   doxazosin mesylate (Cardura), prazosin hydrochloride (Minipress), terazosin hydrochloride (Hytrin).
9. Combined alpha and beta-blockers
   carvedilol (Coreg), labetolol hydrochloride (Normodyne, Trandate).
10. Central agonists
    alpha methyldopa (Aldomet), clonidine hydrochloride (Catapres), guanabenz acetate (Wytensin), guanfacine hydrochloride (Tenex).
11. Peripheral adrenergic inhibitors
    guanadrel (Hylorel) guanethidine monosulfate (Ismelin), reserpine (Serpasil).
12. Blood vessel dilators
    hydralazine hydrocholoride (Apresoline), minoxidil (Loniten).

The preferred mode of the invention is the combination of lisinopril 20 mg and Liposomal glutathione 800 mg (2 teaspoons). Additional preferences include the other agents in the Angiotensin Converting Enzyme (ACE) Inhibitor category of drugs.

The invention, liposomal glutathione, is also proposed in combination with the nitric oxide enhancing agents such as the nutrients 1-arginine and 1-lysine in order to facilitate the formation of GSNO, which is needed for vasodilation.

It is proposed that the invention, liposomal glutathione, in combination with an antihypertensive agent such as lisinopril and arginine to allow a more efficient blood pressure lowering using a lower dose of the antihypertensive agent as illustrated in example 5.

The liposomes and the encapsulation of reduced glutathione used in the current invention are described in Guilford, U.S. patent application Ser. No. 11/163,979 filed Nov. 6, 2005, published May 11, 2006 as 20060099244 which is incorporated in its entirety. While the preferred embodiment of the invention is the preferred embodiment listed in Guilford, U.S. patent application Ser. No. 11/163,979, the other methods of liposomal encapsulation of the invention as described in Guilford, U.S. patent application Ser. No. 11/163,979 as well as in Keller et al, U.S. Pat. No. 5,891,465, Apr. 6, 1999, Keller et al U.S. Pat. No. 6,958,160, Oct. 25, 2005, and Keller US Patent application 20020039595, published Apr. 4, 2002 are incorporated into this description.

The current application is prompted after reviewing the unpublished findings of a study on the activity of a liposomal encapsulation of reduced glutathione on the stabilization of cholesterol, LDL and HDL when they were exposed to agents known to create rapid oxidation of these materials. As will be reviewed, the oxidation of Low Density Lipoprotein (LDL) with the oxidized LDL referred to as oxLDL, is significantly slowed by the addition of liposomal reduced glutathione, the current invention, which utilizes glutathione peroxidase as a key to enable reduced glutathione to function to prevent oxidation of cholesterol. Exporting reduced glutathione effectively into the blood system and into cells has not been previously feasible except by intravenous means. By liposomal encapsulation, this invention enables that export of reduced glutathione into the blood system making it available to cells d and cell membranes. The liposomal encapsulation also allows the availability of that reduced glutathione to cooperate with Glutathione Peroxidase to impeded undesired oxidation of LDL and HDL cholesterol. In the presence of high fat diet or high lipid content of blood, the normal glutathione formation capacity of the system is often exceeded requiring an outside source of intracellular glutathione to maintain the antioxidant status of the system. This invention provides a novel and surprising answer to prevent or slow the oxidation of LDL, which is associated with atherosclerosis.

As related in the unpublished Aviram study, the novel finding of glutathione peroxidase related to native cholesterol, HDL and LDL suggests that the availability of reduced glutathione is critical for maintaining the normal state of function of these materials. Other antioxidants may provide indirect support for this function, but reduced glutathione functions much more efficiently.

FIGURES

FIGS. 1A and 1B show the results of the effect of Liposomal Glutathione on LDL oxidation by incubation of LDL with increasing concentrations (0-12 µg/mL) of Liposomal Glutathione resulted in a significant inhibition in the extent of $CuSO_4$ (5 µmol/L)-induced LDL oxidation, as measured by the TBARS assay (FIG. 1A), or by the lipid peroxides assay (FIG. 1B). The maximal inhibitory effects by 88% (TBARS) or by 92% (lipid peroxides) were noted upon the addition of 2.5 µg/ml of Liposomal Glutathione to the LDL oxidation system (FIG. 1A and FIG. 1B). In contrast, the addition of similar concentrations of the Control Liposome (with no glutathione) to LDL in the presence of copper ions, did not significantly affect the extent of LDL oxidation, as measured by the TBARS assay (FIG. 1A) and also by the lipid peroxides assay (FIG. 1B).

FIGS. 1C and 1D show Liposomal reduced glutathione in the Liposomal Glutathione solution also significantly inhibited LDL oxidation in a dose-dependent manner, as measured by the time required for conjugated dienes formation (FIG. 1C and FIG. 1D). The addition of 2 µg/ml of Liposomal Glutathione to LDL resulted in the prolongation of the lag time from 40 minutes in control LDL (incubated with no addition), up to 91 minutes observed for LDL that was incubated with Liposomal Glutathione (FIG. 1C and FIG. 1D).

Figure 2:
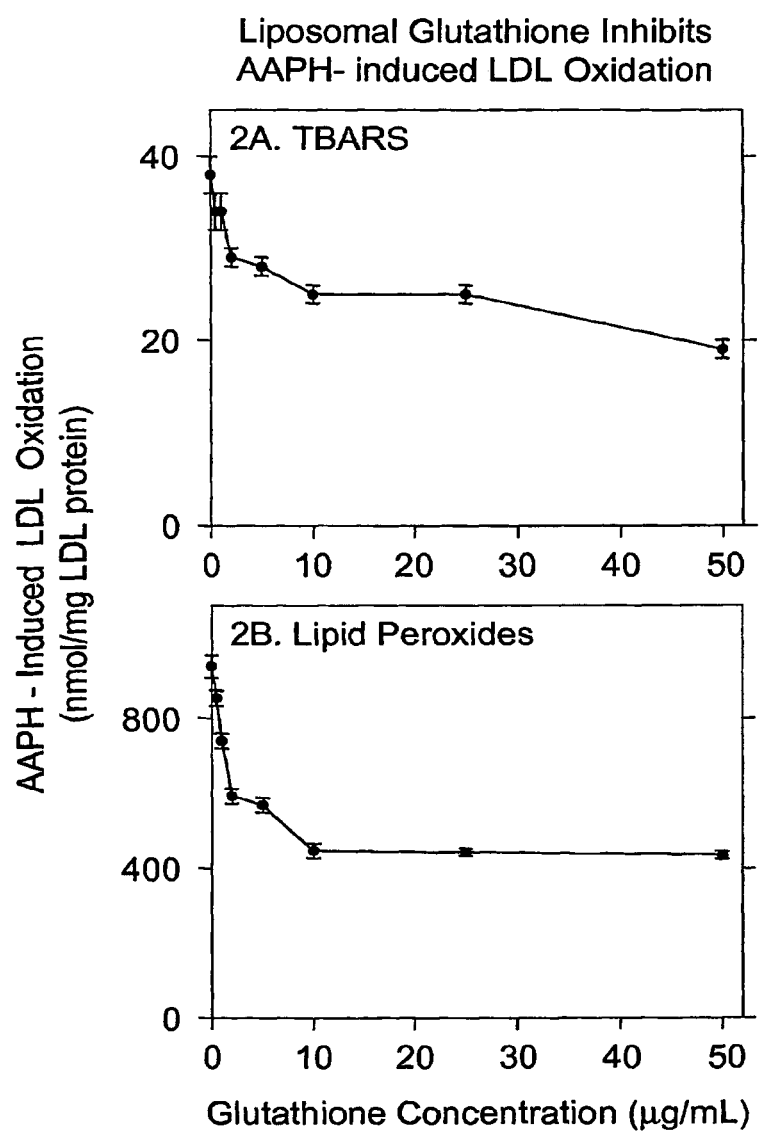

FIGS. 2A and 2B shows the results of addition of increasing concentrations (0-50 µg/ml) of Liposomal Glutathione to LDL, which significantly decreased the susceptibility of LDL to oxidation induced by 5 mmol/L AAPH, by up to 50% and 54%, as measured by the TBARS (FIG. 2A), or by the lipid peroxides (FIG. 2B) assays, respectively.

Figure 3:
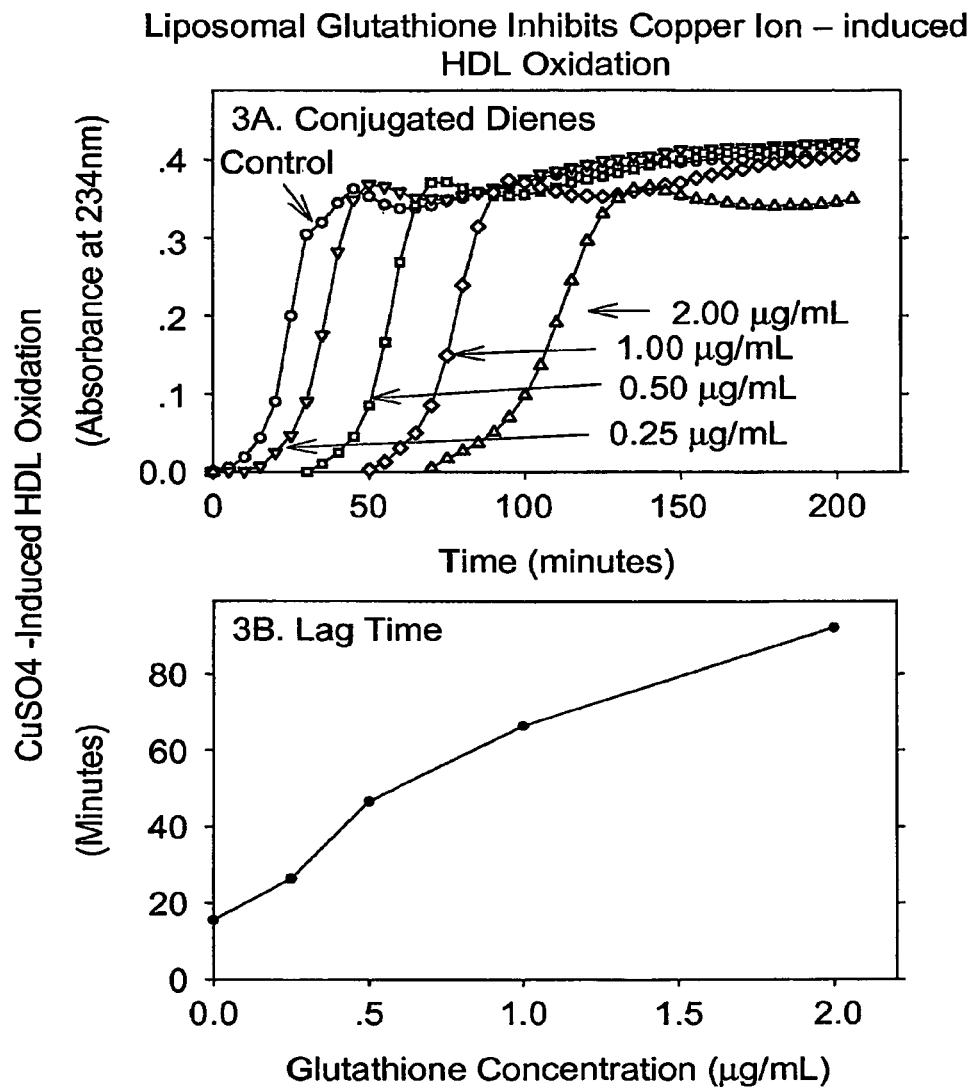

FIGS. 3A and 3B show the effect of Liposomal Glutathione on HDL oxidation by incubation of HDL with increasing concentrations (0-2 µg/mL) of Liposomal Glutathione significantly inhibited, in a dose-dependent manner, the susceptibility of the HDL to copper ion-induced oxidation, as determined by the lag time required for conjugated dienes formation (FIG. 3A and FIG. 3B). The addition of 2 µg/mL Liposomal Glutathione to HDL resulted in prolongation of the lag time from 16 minutes in control HDL (incubated with no additions) up to 92 minutes observed for HDL that was incubated in the presence of Liposomal Glutathione.

Figure 4:
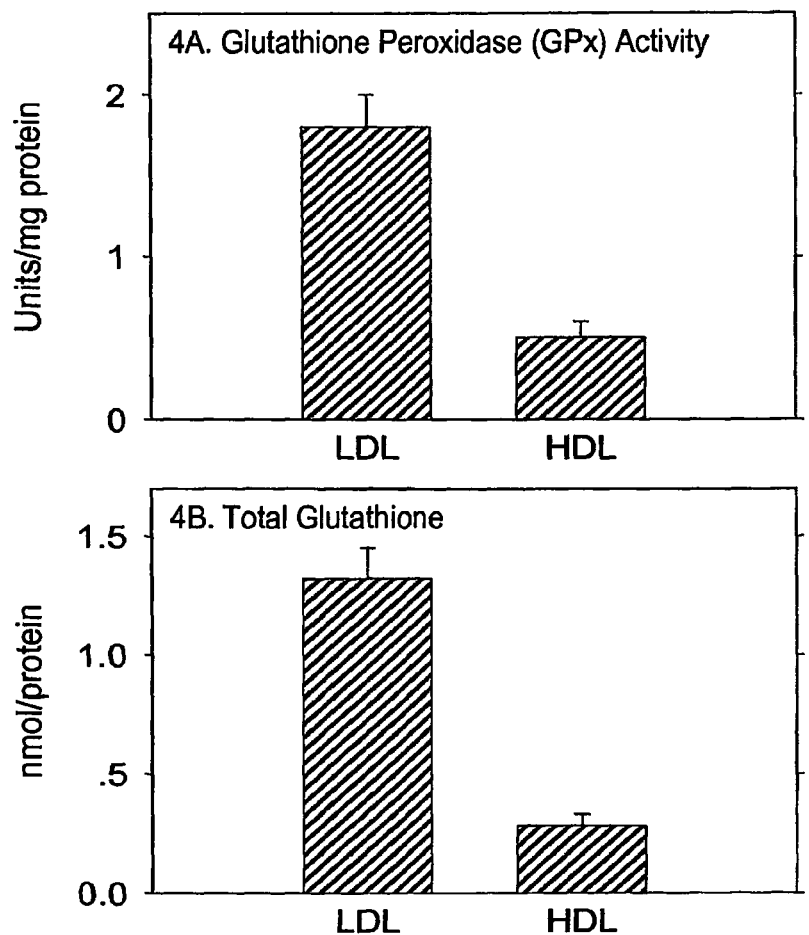

FIG. 4 shows that GPx activity in LDL was about 5 fold higher than the activity observed in HDL (FIGS. 4A and 4B). In parallel, both lipoproteins were shown to contain glutathione. Lipoprotein-associated glutathione level in LDL was again shown to be higher, by about 4 fold, in comparison to its level in HDL (FIG. 4B).

FIG. 5 shows what the inventor describes the "taurine shunt" for the described switch in biochemical pathways. The abbreviations in FIG. 5 are as follows: THF: tetrahydrofolate; MS: methionine synthase; BHMT: betaine-homocysteine methyltransferase; MAT: methionine adenosyltransferase; SAM: S-adenosylmethionine; SAH: S-adenosylhomocysteine; SAHH: SAH hydrolase; ADA: adenosine deaminase; AK: adenosine kinase; CBS: cystathionine beta synthase; B12: cyanocobalomine; meB12: methylcobalamine; 5-CH$_3$ THF: 5-Methyltetrahydrofolate.

OBJECTIVES OF THE INVENTION

It is an objective of the invention to simultaneously alter in a therapeutic way the oxidation state of LDL and HDL and thereby inhibit and reverse the tendency to vascular disease and associated events.

It is an objective of the invention to enable a therapeutic response from the management of the LDL to a concern about the management of the oxidation state of LDL and thereby diminish a trigger for developing atherosclerosis.

It is an object of the invention to maintain normal antioxidant function in LDL and to maintain the normal antioxidant function of HDL by reduced glutathione and thus maintain normal artery function and avoid atherosclerosis.

It is an object of the present invention to offer a composition that can be utilized orally, mucosally, intravenously, or topically that enables an absorbable material capable of intracellular absorption to supply the physiologic substrate needed to work with glutathione peroxidase in the maintenance of normal artery lining cell function and potentially slow, stop or reverse vascular disease by deterring creation of Oxidized LDL or HDL.

It is an object of the invention to enable effective cellular delivery of reduced glutathione by liposomes to bypass mechanisms that favor taurine production over glutathione production.

It is an object of the invention to utilize liposomal reduced glutathione in order to enable the use of lower doses of the statin class of cholesterol-lowering drugs while maintaining efficacy of statins and reducing side effects of statins.

DESCRIPTION

It is proposed that the continued oral usage of the current invention, liposomal reduced glutathione, will maintain reduced glutathione as prevention against the damage that can occur with low glutathione levels. The continuous daily ingestion of an exogenous source of reduced glutathione in the form of liposomal glutathione is proposed as a method of prevention of atherosclerosis and vascular disease and as a treatment for individuals at risk of progression of existing atherosclerosis, vascular disease or vascular associated difficulties such as erectile dysfunction. Again, vascular disease, for purposes of specification of the invention, is intended to include vascular disease generally, and to specifically include atherosclerosis, diabetes, hypertension, narrowing of arteries leading to decreased blood flow, ischemic events, and the formation of blood clots, abnormal platelet aggregation, and thrombotic events. The use of the term "glutathione" or "glutathione (reduced)" will refer to biochemically reduced glutathione as opposed to oxidized glutathione, or glutathione that is in the biochemically oxidized state.

In order to examine the problems presented by the background which follows, one inventor inaugurated a study as yet unpublished called: "The effect of liposomal glutathione on the oxidation of the cholesterol components known as Low density lipoprotein (LDL) and high density lipoprotein (HDL)." Observations with respect to the interaction between glutathione peroxidase, liposomal reduced glutathione, and HDL and LDL led to this invention. In particular, the study highlighted the importance of reduced glutathione in maintaining the normal state of function of HDL and LDL, apparently by lowering the oxidation state of LDL and HDL.

Example 1

An unpublished study of "The effect of liposomal glutathione on the oxidation of the cholesterol components known as Low density lipoprotein (LDL) and high density lipoprotein (HDL)" was performed by Professor Michael Aviram The Lipid Research Laboratory Rambam Medical Center, Haifa Israel, which demonstrates the novelty of the invention and its effect on LDL oxidation and on HDL oxidation.

Methods

Liposomal Glutathione composition: The Liposomal Glutathione solution consisted of: 8.25% reduced glutathione (GSH, 84.5 mg/mL), 75.15% deionized water, 15% glycerine, 1.5% lecithin, and 0.1% potassium sorbate (on a % weight/weight basis). Control Liposomes consisted of similar composition, but without reduced glutathione. Lipoproteins isolation: Low density lipoprotein (LDL) and high density lipoprotein (HDL) were isolated from the serum of normolipidemic volunteers by density gradient ultracentrifugation. The LDL and HDL protein concentration was determined by the Lowry method.

LDL and HDL oxidation studies—Before oxidation the lipoproteins were dialyzed against PBS. LDL or HDL (100 µg of protein/mL) were incubated with 5 µmol/L of CuSO4 for 3 hours at 37° C., or with 5 mmol/L of the free radical generator 2,2-azobis 2, amidinopropane hydrochloride (AAPH). The lag time required for initiation of LDL or HDL oxidation is determined by continuous monitoring of conjugated dienes formation (by measuring the optical absorbance at 234 nm). The extent of LDL oxidation would be determined also by measuring the amount of LDL-associated lipid peroxides or thiobarbituric acid reactive substances (TEARS).

Glutathione peroxidase (GPx) activity—GPx activity in HDL (1.3 mg protein/mL) or in LDL (0.5 mg protein/mL) was measured according to the method of Thomas J P et al, (J. Biol Chem, 265:454-461, 1990), using 1004 of the lipoproteins. The reaction mixture include: 1 mol/L Tris-HCl buffer pH 8.0+5 mmol/L EDTA, 0.1 mol/L reduced glutathione, 10 units/mL of glutathione reductase, 2 mmol/L NAD(P)H, and t-butylhydroperoxide (diluted 1:1000, v:v with water).

Total glutathione determination in LDL and HDL—All the preparation steps were performed on ice. The HDL and the LDL were treated with sulfosalycylic acid and the samples were centrifuged. The total glutathione levels were measured in the supernatant by the DTNB-GSSG reductase recycling assay.

Results of the effect of Liposomal Glutathione on LDL oxidation incubation of LDL with increasing concentrations (0-12 µg/mL) of Liposomal Glutathione resulted in a significant inhibition in the extent of $CuSO_4$ (5 µmol/L)—induced LDL oxidation, as measured by the TBARS assay (FIG. 1A), or by the lipid peroxides assay (FIG. 1B). The maximal inhibitory effects by 88% (TBARS) or by 92% (lipid peroxides) were noted upon the addition of 2.5 µg/ml of Liposomal Glutathione to the LDL oxidation system (FIG. 1A and FIG. 1B). In contrast, the addition of similar concentrations of the Control Liposome (with no glutathione) to LDL in the presence of copper ions, did not significantly affect the extent of LDL oxidation, as measured by the TBARS assay (FIG. 1A) and also by the lipid peroxides assay (FIG. 1B).

Liposomal reduced glutathione in the Liposomal Glutathione solution also significantly inhibited LDL oxidation in a dose-dependent manner, as measured by the time required for conjugated dienes formation (FIG. 1C and FIG. 1D). The addition of 2 µg/ml of Liposomal Glutathione to LDL resulted in the prolongation of the lag time from 40 minutes in control LDL (incubated with no addition), up to 91 minutes observed for LDL that was incubated with Liposomal Glutathione (FIG. 1C and FIG. 1D).

Similarly, addition of increasing concentrations (0-50 µg/ml) of Liposomal Glutathione to LDL, significantly decreased the susceptibility of LDL to oxidation induced by 5 mmol/L AAPH, by up to 50% and 54%, as measured by the TBARS (FIG. 2A), or by the lipid peroxides (FIG. 2B) assays, respectively.

The effect of Liposomal Glutathione on HDL oxidation

Incubation of HDL with increasing concentrations (0-2 µg/mL) of Liposomal Glutathione significantly inhibited, in a dose-dependent manner, the susceptibility of the HDL to copper ion-induced oxidation, as determined by the lag time required for conjugated dienes formation (FIG. 3A and FIG. 3B). The addition of 2 µg/mL Liposomal Glutathione to HDL resulted in prolongation of the lag time from 16 minutes in control HDL (incubated with no additions) up to 92 minutes observed for HDL that was incubated in the presence of Liposomal Glutathione.

Suggested mechanism by which Liposomal Glutathione inhibits copper ion-induced LDL and HDL oxidation.

As glutathione peroxidase (GPx) is present in serum, and it converts lipid peroxides to alcohols by using reduced glutathione in order to reactivate GPx (as a result of its reduction), the question was presented whether GPx is present in lipoproteins (LDL and HDL), which were isolated from human serum.

Indeed, for the first time, the presence was noted of GPx activity in LDL and to a lesser extent in HDL. GPx activity in LDL was about 5 fold higher than the activity observed in HDL (FIGS. 4A and 4B). In parallel, both lipoproteins were shown to contain glutathione. Lipoprotein-associated glutathione level in LDL was again shown to be higher, by about 4 fold, in comparison to its level in HDL (FIG. 4B).

In reviewing the results, it appears that LDL and HDL contain both the enzyme glutathione peroxidase (GPx) and it specific substrate reduced glutathione. The presence of GPx associated with LDL has not previously been reported. Thus the native lipids, as obtained from human subjects contain the mechanism to maintain defense against oxidants and to maintain a non-oxidized state. When materials known to cause oxidation are added to this system, there is a brief resistance to oxidation, but when the native glutathione is used up oxLDL is created. The surprising finding that leads to this invention is that the addition of even a small amount, 2 µg/mL, of the liposomal encapsulated reduced glutathione results in a prolonged stabilization of the lipids against the oxidizers. The addition of 2 µg/mL Liposomal Glutathione to HDL resulted in prolongation of the lag time from 16 minutes in control HDL (incubated with no additions) up to 92 minutes observed for HDL that was incubated in the presence of Liposomal Glutathione.

In the human system, there is a finite amount of reduced glutathione available that continually supplies in conjunction with glutathione peroxidase, the protection against production of oxidized LDL. When the oxidizer stressors overwhelm the production of reduced glutathione this invention proposes that the oxidation of LDL will be delayed and avoided by the addition of a convenient outside source of reduced glutathione and enable HDL to continue its cholesterol removal. The specificity of the enzyme glutathione peroxidase for chemical interaction with reduced glutathione only explains why there has not previously been a consistent response to antioxidant therapy for atherosclerosis in human studies.

Other antioxidants may provide indirect support for normal function, but reduced glutathione functions much more efficiently and effectively. Further, the inventors determined that synergistic effect from liposomal reduced glutathione could be achieved by potentially using lower doses of statins that usually required, reducing side effects while sustaining. Moreover, the addition of CoQ10 or ubiquinone could ameliorate one of the side effects of statins.

Example 2

CP is an 11 year old boy who presented with a 6 month history of persisting fatigue. Prior to his illness, he was actively involved with school and sports. In sports he ran cross country, played soccer and baseball. At the time of his initial evaluation, his activity was restricted to partial days at school and no physical activity. With physical activity he became exhausted and was not able to keep up his school work. The onset of his symptoms in the spring of the year coincided with what were thought to be cold symptoms with recurring rhinitis followed by an ear infection in the late summer. He had seasonal allergies, which started 2 years prior to the current illness.

At the initial evaluation the working diagnosis was chronic viral illness related to Epstein-Barr Virus (EBV). His physical exam revealed nasal congestion with inflammation of the nasal mucosa and an enlarged spleen. His viral antibody evaluation revealed significant elevations of:

IgG Antibody to EBV capsid antigen of 5.4–normal<0.9=Elevated
  IgM Antibody to EBV capside antigen of 0.05–normal<0.9=Negative
  IgG Antibody to EBNA (Epstein Barr Nuclear Antigen) 4.35–normal<0.9=Elevated The interpretation of the results of the EBV antibody tests were consistent with a past EBV infection. However, a month later, Dec. 1, 2005 his IgG Antibody to EBV capsid antigen increased to 6.14. As the patients anti-EBV viral titers were continuing to rise, consistent with his continued fatigue and consistent with the diagnosis of chronic viral syndrome related to EBV.

CP's remaining lab tests were normal including a normal CBC with a mild elevation of eosinophils at 6% (normal <5). The eosinophilic cationic protein level was 13.5 ng/ml (1.5-5.5), a finding consistent with inflammation such as allergy. Red Blood Cell glutathione level was 128 µmole/L (200-400 µmole/L) and the plasma glutathione level was 140 (200-400 µmole/L).

Urine taurine level was significantly elevated at 1485 µmole/gm creatinine) with normal 150-300 µmole/gm creatinine.

While blood levels for mercury, lead and arsenic were within normal limits it was elected to assess further for the possible presence of mercury as there was no explanation for the low glutathione level. A DMPS challenge for mercury revealed a significant elevation of mercury at 32 µg/gm creatinine excreted in the urine after an infusion of 5 cc of DMPS. Normal is considered to be 10-12 µg/gm creatinine, even though theoretically, there should be no mercury excreted in the urine as this is a toxin and there is no known metabolic function for this metal. An unprovoked urine sample revealed a mercury level of 1.3 µg/gm creatinine This method is an adaptation of the DMPS challenge described by Molin in 1991 (Molin).

CP was treated over the next 5 months with the present invention, liposomal reduced glutathione, two teaspoons per day, equivalent to a total of about 800 mg. per day and a series of DMPS infusions. After six months, his mercury level was still elevated at 23 µg/gm creatinine. The DMPS therapy was continued and two months later, his mercury excretion was found to be 10 µg/gm creatinine.

Repeat testing of the glutathione and taurine revealed that CP's red blood cell (RBC) glutathione was 378 µmole/L (200-400 µmole/L) and the plasma glutathione level was 310 (200-400 µmole/L). The urine taurine level had decreased to 23.7 µmole/gm creatinine.

At the conclusion of the therapy CP had returned to school full time, has resumed cross country training and at the same time is playing on a soccer team.

The preferred embodiment for the invention in regard to the detoxification of mercury is the use of the liposomal glutathione in doses of 100 mg for every 30 pounds (15 kg) twice a day. For individuals over 100 pounds dosing is 1 teaspoon=400 mg twice a day. The dose of DMPS is 5 mg/kg. for an oral dose. If it convenient to give an intravenous infusion a dose of 3.5 mg/kg can be used. For adults or children over 100 pounds an initial dose of 125 mg is given to determine tolerance to the material. If tolerated, then a treatment dose of 250 mg may be considered. Urine for toxic metal (mercury) analysis is obtained for 6 hours after the infusion. In the preferred embodiment of this protocol, the glutathione level is supported using the liposomal glutathione, for 2 weeks prior to the infusion of DMPS.

Example 3

Patient C is a 67 year old in the late stages of prostate cancer, who became depressed, weak and wanted to die. His condition was and is terminal and all therapy and most supportive care had been withdrawn. He was down to sips of water for days on end. Patient C was given the current invention, liposomal glutathione (reduced) one teaspoon Three times a day (400 mg. per teaspoon) for a total of 1200 mg per day. Each teaspoon was diluted in 2 ounces of apple juice. 10 hours later; the next day, the patient was observed to have a significant improvement in general outlook, reporting a significant lessening of depression and pain, and over-all vigor that led to a dramatic improvement in his condition that lasted for several days. Unfortunately, this effect was not permanent. The improvement observed lasted about 6 days.

For background information on the effect of liposomal glutathione on neurotransmitters, the reader is referred to Guilford U.S. patent Ser. No. 11/420,168 filed May 24, 2006.

Example 4

AF, a 67 year old man with another form of vascular disease, hypertentions, presents with continued elevation of blood pressure in the range of 190/100 to 210/110. The high blood pressure was attributed to an upper respiratory infection and anxiety. On the follow up visit, two weeks later, the pressure remained elevated. While considering medication, AF elected to start arginine 450 mg capsule in combination with liposomal glutathione 800 mg, in a liquid form. Beginning the next morning, his blood pressure was measured at 150/90. While maintaining this regimen, his blood pressure has fluctuated somewhat remained in the 160/90 area.

Example 5

MR, a 60 year old woman, with diabetes requiring insulin therapy also has a long history of elevated blood pressure. The blood pressure was previously controlled using lisinopril 20 mg. daily. Her blood pressure then became uncontrolled with readings of 188/92. The dose of lisinopril was increased to 20 mg twice a day, which over 3 days brought her blood pressure down to 145/92. MR was started on one 1-arginine 450 mg. per capsule in combination with 800 mg liposomal glutathione in its liquid form. The next day her blood pressure was 130/74. The dose of lisinopril was lowered to 20 mg once a day. Continuing the arginine and liposomal glutathione, the blood pressure remains stable at 130/74.

The current invention proposes the use of reduced l-glutathione delivered in a liposomal encapsulation as a therapeutic to ameliorate the oxidation stress that leads to the formation of atherosclerosis. The liposome encapsulated l-reduced glutathione will be referred to as Reduced Liposomal Glutathione. The term glutathione will be used to refer to the biochemically reduced stated of glutathione. The liposomal formulation is available from BioZone Laboratories, Inc. of Pittsburgh, Calif. for use with the glutathione (reduced) and other pharmaceutical agents referenced in the invention. The liposomal glutathione (reduced) in the preferred formulation is available from Your Energy Systems, LLC. of Palo Alto, Calif. That formulation of liposomal glutathione (reduced) produced with BioZone liposomes by Your Energy Systems, LLC can, unlike other formulations, be stored for at least months at room temperature.

The role of reduced l-glutathione in atherosclerosis prevention has previously not been well understood. This is in part because there has heretofore been no method of supplying reduced glutathione to the human system via a convenient, regular method. The use of intravenous glutathione reported by Arosio is too cumbersome and impractical to find routine clinical usage. In previous studies, a liposomal delivery of reduced glutathione has not been available. The present invention offers the substantial advantage of being utilized orally, transdermally, mucosally as well as intravenously.

The recent unpublished study by Michael Aviram, PhD, commissioned by one of the inventors, see example 1, reveals that glutathione peroxidase (GPx) is present in the cholesterol molecules removed from volunteers with normal cholesterol levels. The predominant amount of GPx was found in the LDL fraction of the cholesterol. The administration of even extremely small amounts of the present invention was able to prevent the oxidation of cholesterol and its subcomponents LDL and HDL when they were exposed to materials known to cause oxidation of lipids. The materials used to precipitate lipid oxidation were both a metal of CuSO4 for 3 hours at 37° C., or a chemical oxidizer, 5 mmol/L of the free radical generator 2,2-azobis 2, amidinopropane hydrochloride (AAPH).

The study demonstrates the novel finding that glutathione peroxidase is present in the native state with cholesterol, HDL and LDL. This enzyme is specific for function with reduced glutathione. When the oxidizers affecting the system exceed the availability of the system's glutathione support of the peroxidase, oxidation stress will occur. When the oxidation stress continues and causes irreversible damage to lipids and cell membranes, oxidation damage occurs. The damage to cell membranes eventually spreads to the entire system of tissue of these cells with consequent compromise of organ function and disease. The normal system's production of glutathione to support a high fat environment has been demonstrated to have a finite capacity in animal studies. Short term exposure, 18 days, to high fat diets in rabbits demonstrates that there is an initial increase in the production of glutathione. After a longer period of the diet, 80 days, however, a significant reduction in reduced glutathione was noted (Lapenna). The deficiency in glutathione was also correlated with the appearance of atherosclerotic changes in the rabbit aorta, which were not evident in the animals with normal amounts of reduced glutathione. The results related in Example 1 illustrate that oxidized LDL can be maintained in a normal oxidative state using the present invention, liposomal encapsulated glutathione. This finding suggests that the appearance of the oxidized form of LDL, that precedes atherosclerotic changes in mammals with excess cholesterol or LDL, could be delayed or prevented using liposomal glutathione. This information is also highly suggestive that the current invention, liposomal reduced glutathione in individuals prone to atherosclerosis can delay or prevent the oxidation of LDL and thereby slow that the progression to atherosclerosis, or stop the progression and perhaps reverse it.

It is proposed that the current invention, liposomal reduced glutathione, be used as a therapeutic for prevention of progression of atherosclerosis and potentially for reversal of atherosclerosis by facilitation of HDL activity by preventing HDL oxidation in individuals with evidence of atherosclerosis such as increased intimal thickening, low reduced glutathione levels or abnormal elevation of the ratio of reduced glutathione to oxidized glutathione (gsh/gssg) or other biomarkers of oxidation stress such as oxidized LDL. It is proposed that the invention, liposomal glutathione, also be used in individuals with elevation of cholesterol or LDL or with mammals with increased levels of oxidized LDL. It should also be added to the management plan for the finding of one or more of these additional biomarkers of vascular disease and atherosclerosis, which include Lipoprotein(a), homocysteine, interletikin-6 and tumor necrosis factor receptor, C-reactive protein or fibrinogen (collectively referred to as "Vascular Disease Biomarker." These Vascular Disease Biomarkers are indicators of, and associated with, an increased risk of forming a clot due to vascular disease and impeding blood flow: an occurrence which is known as a thrombotic event.

The novel and surprising finding of the presence of glutathione peroxidase in the cholesterol fraction known as LDL in the study cited in example 1 provides a valuable link in the understanding of the oxidation of LDL. The information cited explains how either excess amounts of cholesterol or LDL leads to the continuous formation of oxidized cholesterol or LDL as elevations of these materials eventually overwhelms the production of reduced glutathione. Thus, elevated levels of cholesterol or elevated levels of oxidized LDL (oxLDL) are both biomarkers of atherosclerosis (Fraley) and direct contributing causes of atherosclerosis. Introducing antioxidants such as vitamin C and vitamin E in humans to slow the oxidation stress has not been as helpful as anticipated (Cynshi). The action of prevention of oxidation of LDL by use of the present invention, liposomal reduced glutathione, provides a composition to directly interact with the glutathione peroxidase, which is the method provided by nature for the stabilization of these lipids and demonstrates a method of preventing and slowing the damage related to oxLDL in a number of disease states as shown in Example 1. For example, It is proposed that the use of the present invention slow or prevent the progression of the arterial damage that occurs related to oxLDL due to the direct protective effect that has demonstrated on human, LDL and HDL as reviewed in the unpublished work presented in Example 1.

Elevations of cholesterol which persist over a period of time have been shown in animal models to deplete the antioxidant capacity of the organism leading to simultaneous events resulting in dysfunction. Elevated cholesterol leads to depletion of glutathione, an excess of oxLDL and a progression of events that can result in tissue Changes and damage such as atherosclerosis as demonstrated in the study of rabbits fed high cholesterol diets for long periods of time (Lapenna). It is proposed that the continued oral usage of the current invention, liposomal reduced glutathione, will maintain reduced glutathione as prevention against the damage that can occur with low reduced glutathione levels, which leads to elevations of oxidized LDL. The present invention is a composition that can be used to provide on a continual basis that is the natural method for preventing the oxidation of LDL. The enzyme glutathione peroxidase that is a major component of this system is a catalyst and effectively can be re-used on a continuing basis, as this is the nature of enzymes. Enzymes provide for the enhancement of a biochemical reaction without being used up. The element in the glutathione related antioxidant system that must be provided for on a continuing basis is reduced glutathione. Normally, the body is able to make glutathione in adequate amounts and have reduced glutathione available in adequate amounts. Situations that cause an increased demand on the glutathione antioxidant system are common in today's world. The normal utilization of oxygen for energy production causes the formation of biochemicals called free radicals that increase oxidation stress, so that even normal exercise can cause oxidation stress. Normally, the body can overcome the "normal" amount of such stressors, but the additional oxidation stress from pollutants or toxins such as toxic metals can increase the demand for production of reduced glutathione. The presence of increased fats in the diet leading to excess cholesterol and LDL will increase the demand for reduced glutathione. Defects or stressors that lead to the biochemical situation described by the "taurine shunt" will lead to the decreased availability of reduced glutathione. In these situations, The continuous daily oral ingestion of an outside source of reduced glutathione in the form of liposomal glutathione is proposed as a method of maintaining the levels of reduced glutathione that are normally present in the system. The availability of reduced glutathione in the system will maintain the normal mechanism for the prevention of oxidation of lipids such as LDL and HDL. This, in turn, prevents the formation of the abnormalities leading to plaque formation and atherosclerosis. Thus, the present invention provides a method for the prevention of atherosclerosis and the many diseases associated with decreased blood flow. It also provides a method for the treatment of individuals at risk of progression of existing atherosclerosis and other organs at risk for damage from decreased blood flow.

Other Organs and Erectile Dysfunction

Vascular disease can affect other organs in addition to the heart (coronary artery disease and heart attack) and brain (cerebral blood flow and stroke). Low density lipoprotein (LDL) exists within the brain and is highly vulnerable to oxidative modification. Oxidized LDL (oxLDL) is capable of causing neuronal cell death in cultures of brain cells known as neurons. Amyloid β-peptide is the peptide found tangled in the brain of individuals with Alzheimer's Disease. Glutamate is a biochemical found in the brain and which is released into the connector area between neurons known as the synapse. Glutamate is an excitatory stimulant neurotransmitter substance that should be rapidly removed and converted to glutamine by the addition of an ammonia group.

Incubating neuronal cells exposed to oxLDL with either amyloid β-peptide or glutamate increased the oxidative stress in neurons, astrocytes, and microglia and resulted in an increase in neuronal death (Keller, 1999). This data suggests that oxLDL may play a role in brain dysfunction such as Alzheimer Disease. Additionally there is data to support the observation that highly oxidized high density lipoprotein (oxHDL) can also induce oxidation stress in neurons, astrocytes, and microglia. The increase in oxidation stress in these brain cells leads ultimately to neuron death. Chemical changes that are associated with oxidation damage have also been identified in the post mortem brain tissues of individuals with Alzheimer's disease (Keller, 2005). It is postulated that oxidative damage may one of the earliest events in the onset and progression of Alzheimer's disease. It is proposed that the present invention be used to prevent the oxidation of LDL and HDL in the brain that precedes the clinical diagnosis of Alzheimer's disease. The present invention is proposed as a preventative for the brain damage that may accompany increased oxidized LDL in the peripheral blood circulation as well as the oxidative changes that occur in the central nervous system and brain circulation. As Example 1 demonstrates, the oxidation of LDL and HDL will clearly be impeded by liposomally encapsulated reduced glutathione.

Because elevated cholesterol is known to be a risk factor developing Alzheimer's disease. It is proposed that the present invention be used in combination with one of the pharmacologic preparations known as statins for the prevention of the oxLDL and oxHDL changes that precede and are associated with Alzheimer's disease. The dosing is the same as those reviewed in the section "Combination with Statin". The preferred preparation is a combination of the liposomal glutathione in combination with a statin that does not cross the blood brain barrier such as pravastatin, which is highly hydrophilic and less likely to cross the blood-brain barrier. The advantage of a statin that does not cross the blood brain barrier is that it will not impair the production of cholesterol needed in the brain for the formation of myelin, the covering of nerves in the brain. Rosuvastatin is also hydrophilic and may be considered for this purpose of providing a statin that does not cross the blood brain barrier to use in combination with liposomal glutathione for a long term therapy. The lipophilic statins include simvastatin, lovastatin, atorvastatin and fluvastatin.

The use of the more hydrophilic statin is proposed as the medication may need to be used for a long period of time, probably years, to avoid the development of Alzheimer's disease and using a statin that does not readily cross the blood brain barrier will reduce the potential for brain related complications. The initial dose for the prevention of Alzheimer's disease is pravastatin 5 mg. and 400 mg of liposomal glutathione.

Recent evidence demonstrates that erectile dysfunction has been statistically and clinically associated with vascular disease and atherosclerosis. It has been reported that an elevation of cholesterol (Kim) as well as the amount of cholesterol relative to the amount of HDL called the Cholesterol/HDL ratio (Eaton) is a significant biomarker for erectile dysfunction. As discussed the elevation of cholesterol without adequate HDL will result in an excess of oxidation of LDL. Thus, oxidized LDL appears to be a significant factor in the pathophysiology of erectile dysfunction and that the present invention should be considered in the management of erectile dysfunction. This observation is supported additionally by the finding that red blood cell glutathione concentrations are significantly lower in individuals with erectile dysfunction (Tagliabue). The same study also confirmed the observation that there is an inverse relationship with the level of reduced glutathione and glucose levels in individuals with diabetes.

It is proposed that the present invention be used in the management of erectile dysfunction both with and without diabetes. It is also proposed that the present invention, liposomal glutathione, be used in conjunction with drugs like Sildenafil (Viagra), Tadalafil (Cialis (TM of Lilly, Inc.)) and Vardenafil (Levitra (TM of Bayer, Inc.)) to increase their efficacy so that a smaller amount of the drug may be used or the present invention, liposomal glutathione be may be used in combination with natural, herbal erectile stimulants such as yohimbine. Yohimbine derived from an African plant and is sold as an herb and muira puma derived from a Brazilian plant (Waynberg). Muira Puma has been reported to have an enhanced effect on desire in both women and men and in combination with the present invention, liposomal glutathione. It is proposed that the combination, with or without gingko biloba, be used in the management of erectile dysfunction in both men and in women with sexual dysfunction. Other herbs of interest in these combinations may include Ashwaganda and Mucuna pruriens. All of the substances that function as erectile stimulants including the substances listed in this paragraph are referred to as "erectile stimulants."

Combination with Statin

The biochemical cycle that produces cholesterol includes a substance called Acetyl-CoA enzyme. It is converted to an intermediate called mevalonate by an enzyme called 3-hydroxy-3-methylglutamate-CoA reductase ("HMG-CoA").

Recent pharmaceutical advances have produced a number of substances that inhibit the activity of HMG-COA and slow the production of cholesterol. HMG-CoA reductase inhibitors have been used and are referenced to be used to reduce cholesterol to slow various blood vessel and related heart disease problems which we generally refer to as cardiovascular disease and atherosclerosis. Current therapy for the treatment of cholesterol elevation is the use of HMG-CoA inhibitors to lessen the production of cholesterol. At the same time, the HMG-CoA reductase inhibitor simvastatin has been shown to produce positive effects in the endothelial lining of blood vessels even independent of its lipid lowering effects. Animals with high cholesterol diets who exhibited continued high serum cholesterol who were administered simvastatin demonstrated a lower rate of production of F(2)-isoprostanes and thiobarbituric acid-reactive substances (TBARS), markers of oxidative stress, than animals who were not treated with simvastatin and maintained on a high cholesterol diet. Arteriosclerosis Thrombosis Vascular Biology January 2001; 21(1):122-8). Simvastatin is an analog of lovastatin, which are both statins produced from aspergillus terreus. The HMG-CoA reductase inhibitors are known as a class of drugs called "statins" and include atorvastatin (brand name Lipitor (TM of Pfizer, Inc.)), fluvastatin (Lescol (TM of Novartis)), lovastatin (Mevacor (trademark of Merck, Inc.)), pravastatin (Pravachol (TM of Bristol-Myers-Squibb, Inc.)), simvastatin (Zocor, trademark of Merck, Inc.), cervistatin (Baycol (trademark of Bayer, Inc.) and rosuvastatin (brand name Crestor (TM of AstraZeneca)). Also included in the term statin are natural statins, including those which can be produced from fermented Chinese red rice and formulated to be a therapeutic statin, including cholestin The presence of the HMG-CoA reductase inhibitor may contribute to moderating the effects of lipid peroxidation by moderating a complex series of biochemical events. An increased activity of the NAD(P)H oxidase, an enzyme associated with biochemical oxidation in the vascular system, has been reported in both animal experiments and human coronary artery disease. It appears to play an important role in the production of Reactive Oxygen Species (ROS). The action of the NAD(P)H oxidase enzyme has also been shown to promote "uncoupling" of the enzyme that produces NO in the endothelial cells, called NO synthase. Nitric oxide is an important component of the vasodilating mechanism. The "uncoupling" this enzyme changes the production of NO to the production of the superoxide radical and not production of nitric oxide. Additionally, the action of an antioxidant enzyme, extracellular superoxide dismutase may be decreased by NAD(P)H oxidase. It is thought that vascular treatment strategies that include statins, angiotensin-converting enzyme (ACE) inhibitor or angiontensin I receptor blockade may exert an antioxidant effect by reducing the availability of NAD(P)H oxidase leading to an increase in extracellular superoxide dismutase activity (Landmesser). This sequence of events apparently then leads to the improved endothelial function observed with these drugs and to the decreased production of lipid oxidations products such as isoprostanes. None of these drugs, which represent the standard therapy at this time, act directly on the glutathione peroxidase enzyme as is demonstrated to occur with the present invention. The administration of the present invention, liposomal glutathione, contributes directly to the stability of lipid membranes by the direct interaction of reduced glutathione with the enzyme glutathione peroxidase which is present with the LDL and HDL cholesterol. This is a novel and surprising mode of action related the present invention.

Further Combination with Ubiquinone (CoQ10)

At the same time that statin drugs have been demonstrated to be effective, they can also create undesirable side effects at a rate that may be higher than previously suspected. A recent, 2006, report of 50 consecutive cardiology patients on statin drug therapy for an average of 28 months were found to have possible adverse effects related to statin drug use (Langsjoen). These side effects include myalgia, fatigue, dyspnea, memory loss and peripheral neuropathy. It is thought that the side effects are due to a decrease in the production of a lipophilic enzyme known as coenzyme Q10 (CoQ10) also known as ubiquinone, due to the inhibition of mevalonate synthesis by the statin. These side effects offer a serious impediment to prolonged use of statin drugs. In addition these side effects may limit the most recent guidelines of the National Cholesterol Education Program which called for more aggressive use of statins to lower LDL levels to at least less than 100 mg/dl for patients at moderate or high risk of cardiovascular disease and to less than 70 mg/dl for patients at high risk of vascular disease (Guthrie). These guidelines have been recommended because of the continued correlation of higher incidence of death from vascular disease at higher levels of cholesterol. Reducing the total amount of LDL does not appear to be the total answer to avoiding atherosclerosis. Thus, the concept that the amount of oxidized LDL may actually be a more important factor than the total amount of LDL in terms of contributing to artery disease is beginning to emerge.

It is proposed that liposomal glutathione be used in combination with statin drugs to allow a lower amount of statin to be needed to provide a preventive effect from cholesterol. The net effect of the combination is to decrease the oxidation of cholesterol to a greater degree than the single effect of the statin alone. Thus the reduction of amount of oxidized cholesterol will result in an improved avoidance of vascular occlusion using a lower amount of the statin drug and avoid the complication of depletion of CoQ10.

The components of the present invention combination would be supplied in either a single liposome containing the HMG-CoA reductase inhibitor and reduced glutathione. Alternatively, the components of the present invention combination would be supplied in either a single liposome containing the HMG-CoA reductase inhibitor and reduced glutathione and CoQ10. Alternatively, the components could also be taken individually, but concurrently in their present pill, capsule or liquid form in order to individualize the amount of each component to the needs of the individual. For the HMG-CoA reductase inhibitor the dose may range from 0.10 to 80 mg/day in a single or divided administration. The dose of CoQ10 may vary from 25 mg to 1 g in single or divided doses. A typical CoQ10 dose for a normal adult (70 kg) would be 100 mg per day. The liposomal reduced glutathione dose may range from 100 mg to 2500 mg per day, with the most common dose expected to be in the range of 400 mg once or twice a day for a average adult. A rule of thumb for the preferred dose to begin treatment would be one-half of a typical starting dose in combination with the liposomal reduced glutathione, such as reduced glutathione of 400 mg twice per day and simvastatin 5 mg.

The dose used in the combination of statin and liposomal reduced glutathione is 10 mg of simvastatin once a day and 400 mg of liposomal glutathione administered in two divided doses. Another preferred combination would be It is proposed that the present invention, liposomal glutathione may be used as a sole therapeutic to ameliorate the oxidation of cholesterol, HDL and LDL and to lessen the risk of vascular accident. It has been found in the past that the lowering of cholesterol will result in a decreased risk of vascular accident, but there has been no previous recommendation of a substance or combination to reverse the oxidation state of lipids in the prevention of vascular accidents.

It is proposed that the current invention, liposomal glutathione be combined with CoQ10 either as individual dosed materials or combined in a liposomal encapsulation for the reduction of incidence of vascular accident and atherosclerosis.

It is proposed that the combination of liposomal glutathione combined with CoQ10 be used to ameliorate the effects of low CoQ10 whether this is spontaneously occurring or related to the use of statin medications.

It is proposed that liposomal glutathione be combined with CoQ10 and a statin for the purpose of reducing side effects of such as myopathy associated with statin therapy for reduction of cholesterol. An additional application of this combination is for the amelioration of the effects of oxidized cholesterol, and or oxidized HDL and/or oxidized LDL cholesterol. A review reveals neither a specific references for the use of the combination of glutathione nor reduced and CoQ10 nor the combination of reduced glutathione and CoQ10, nor the use of liposomal encapsulation of reduced glutathione and CoQ10 for management of vascular disease.

For patients on an existing regiment of a statin therapy, the administration of liposomal reduced glutathione combined with CoQ10 is proposed according to the dosages recommended above.

As reviewed in examples 4 and 5, the liposomal glutathione is effective in combination with either a nutrient that increases nitric oxide such as arginine or lysine or in combination with a prescription medication such as lisinopril in combination with arginine and the liposomal glutathione.

The preferred dose of the combination of the invention, liposomal glutathione, and arginine is liposomal glutathione 800 mg in combination with each 450 mg capsule of arginine. This combination may be taken once or twice a day as needed to maintain a normal blood pressure.

The preferred combination of the invention in combination with blood pressure medication is with lisinopril 20 mg daily, in combination with 800 mg of liposomal glutathione. This may be combined with arginine 450 mg as needed. The preferred mode of the invention is the combination of lisinopril 20 mg and Liposomal glutathione 800 mg (2 teaspoons). Additional preferences include the other agents in the Angiotensin Converting Enzyme (ACE) Inhibitor category of drugs.

The invention, liposomal glutathione, is also proposed in combination with the nitric oxide enhancing agents such as the nutrients 1-arginine and 1-lysine in order to facilitate the formation of GSNO, which is needed for vasodilation.

It is proposed that the invention, liposomal glutathione, in combination with an antihypertensive agent such as lisinopril and arginine to allow a more efficient blood pressure lowering using a lower dose of the antihypertensive agent as illustrated in example 5.

The invention is not meant to be limited to the disclosures, including best mode of invention herein, and contemplates all equivalents to the invention and similar embodiments to the invention for humans and mammals and veterinary science. Applications by the inventor Guilford referenced herein are adopted by reference to the extent necessary needed to supplement the specification and to understand the invention and claims.

REFERENCES

References

Arosio E, De Marchi S, Zannoni M, Prior M, Lechi A. Effect of glutathione infusion on leg arterial circulation, cutaneous microcirculation, and pain-free walking distance in patients with peripheral obstructive arterial disease: a randomized, double-blind, placebo-controlled trial Mayo Clinic Proceedings. 2002 August; 77(8):754-9 PMID: 12173710

Ashfaq S, Abramson J L, Jones D P, Rhodes S D, Weintraub W S, Hooper W C, Vaccarino V, Harrison D G, Quyyumi A A. The relationship between plasma levels of oxidized and reduced thiols and early atherosclerosis in healthy adults. J Am Coll Cardiol. 2006 Mar. 7; 47(5):1005-11. Epub 2006 Feb. 9. PMID: 16516085

Bayir H, Kagan V E, Tyurina Y Y, Tyurin V, Ruppel R A, Adelson P D, Graham S H, Janesko K, Clark R S, Kochanek P M. Assessment of antioxidant reserves and oxidative stress in cerebrospinal fluid after severe traumatic brain injury in infants and children. Pediatric Research. 2002 May; 51(5):571-8. PMID: 11978879

Blankenberg S, Rupprecht H J, Bickel C, Torzewski M, Hafner G, Tiret L, Smieja M, Cambien F, Meyer J, Lackner K J; AtheroGene Investigators. Glutathione peroxidase 1 activity and cardiovascular events in patients with coronary artery disease, N Engl J. Med. 2003 Oct. 23; 349(17):1605-13. PMID: 14573732

Bravi M C, Armiento A, Laurenti O, Cassone-Faldetta M, De Luca O, Moretti A, De Mattia G. Insulin decreases intracellular oxidative stress in patients with type 2 diabetes mellitus. Metabolism. 2006 May; 55(5):691-5. PMID: 16631447

Cejas P, Casado E, Belda-Iniesta C, Castro J D, Espinosa E, Redondo A, Sereno M, Garcia-Cabezas M A, Vara J A, Dominguez-Caceres A, Perona R, Gonzalez-Baron M. Implications of oxidative stress and cell membrane lipid peroxidation in human cancer (Spain) Cancer Causes Control. 2004 September; 15(7):707-19. PMID: 15280629

Castelli W P, Garrisoin R J, Wilson P W F, et al. Incidence of coronary heart disease and lipoprotein cholesterol levels: the Framingham Study. Journal of the American Medical Association 1986; 256:2835-8.

Clarke R, Armitage J. Antioxidant vitamins and risk of cardiovascular disease. Review of large-scale randomised trials. Cardiovasc Drugs and Therapy. 2002 September; 16(5):411-5. Review. PMID: 12652110

Crouse J R 3rd, Tang R, Espeland M A, Terry J G, Morgan T, Mercuri M. Associations of extracranial carotid atherosclerosis progression with coronary status and risk factors in patients with and without coronary artery disease. Circulation. 2002 Oct. 15; 106(16):2061-6. PMID: 12379574

Cynshi O, Stocker R. Inhibition of lipoprotein lipid oxidation. Handbook Experimental Pharmacology. 2005; (170):563-90. Review. PMID: 16596815

Di Re F, Bohm S, Oriana S, Spatti G B, Pirovano C, Tedeschi M, Zunino F. High-dose cisplatin and cyclophosphamide with glutathione in the treatment of advanced ovarian cancer. Annals of Oncology. 1993 January; 4(1):55-61. PMID: 8435364

Dursun E, Dursun B, Suleymanlar G, Ozben T. Effect of haemodialysis on the oxidative stress and antioxidants in diabetes mellitus. Acta Diabetologica. 2005 October; 42(3):123-8. PMID: 16258735

Eaton C B, Liu Y L, Mittleman M A, Miner M, Glasser D B, Rimm E B. A retrospective study of the relationship between biomarkers of atherosclerosis and erectile dysfunction in 988 men. International Journal Impotence Research. 2006 Aug. 17; [Epub ahead of print] PMID: 16915303

Ferroni P, Basili S, Paoletti V, Davi G. Endothelial dysfunction and oxidative stress in arterial hypertension. Nutr Metabolism and Cardiovascular Disease. 2006 April; 16(3):222-33. Epub 2006 Mar. 24. Review. PMID: 16580590

Fraley A E, Tsimikas S. Clinical applications of circulating oxidized low-density lipoprotein biomarkers in cardiovascular disease. Current Opinion in Lipidology. 2006 October; 17(5):502-9. PMID: 16960498

Guthrie R M. How safe is aggressive statin therapy? Prog Cardiovasc Nurs. 2006 Summer; 21(3):140-5. PMID: 16957460

Hasnain B I, Mooradian A D. Recent trials of antioxidant therapy: what should we be telling our patients? Cleveland Clinic Journal of Medicine. 2004 April; 71(4):327-34. Review. PMID: 15117174

Hussein O, Rosenblat M, Refael G, Aviram M. Dietary selenium increases cellular glutathione peroxidase activity and reduces the enhanced susceptibility to lipid peroxidation of plasma and low-density lipoprotein in kidney transplant recipients. Transplantation. 1997 Mar. 15; 63(5):679-85. PMID: 9075838

Irshad M, Chaudhuri P S. Oxidant-antioxidant system: role and significance in human body. Indian J Exp Biol. 2002 November; 40(11):1233-9. PMID: 13677624

Jung Y S, Kwak H E, Choi K H, Kim Y C. Effect of acute ethanol administration on S-amino acid metabolism: increased utilization of cysteine for synthesis of taurine rather than glutathione. Adv Exp Med Biol. 2003; 526:245-52. PMID: 12908607

Keller J N, Hanni K B, Markesbery W R. Oxidized low-density lipoprotein induces neuronal death: implications for calcium, reactive oxygen species, and caspases. J. Neurochem. 1999 June; 72(6):2601-9. PMID: 10349872

Keller J N, Hanni K B, Kindy M S. Oxidized high-density lipoprotein induces neuron death. Exp Neurol. 2000 February; 161(2):621-30. PMID: 10686081

Keller I N, Schmitt F A, Scheff S W, Ding Q, Chen Q, Butterfield D A, Markesbery W R. Evidence of increased oxidative damage in subjects with mild cognitive impairment. Neurology. 2005 Apr. 12; 64(7):1152-6. PMID: 15824339

Kim S. Hyperlipidemia and erectile dysfunction. Asian Journal Andrology. 2000 September; 2(3):161-6. Review. PMID: 11225973

Kontush A, Chapman M J. Functionally defective high-density lipoprotein: a new therapeutic target at the crossroads of dyslipidemia, inflammation, and atherosclerosis. Pharmacol Rev. 2006 September; 58(3):342-74. PMID: 16968945

Kunitake S T, Jarvis M R, Hamilton R L, Kane J P. Binding of transition metals by apolipoprotein A-I-containing plasma lipoproteins: inhibition of oxidation of low density lipoproteins. Proc Natl Acad Sci USA. 1992 Aug. 1; 89(15): 6993-7. PMID: 1495991

Landmesser U, Harrison D G, Drexler H. Oxidant stress—a major cause of reduced endothelial nitric oxide availability in cardiovascular disease. Eur J Clin Pharmacol. 2006 February; 62 Suppl 13:13-9. PMID: 16220322

Langsjoen P H, Langsjoen J O, Langsjoen A M, Lucas L A. Treatment of statin adverse effects with supplemental Coenzyme Q10 and statin drug discontinuation. Biofactors. 2005; 25(1-4):147-52. PMID: 16873939

Lavie C J, Milani R V. National Cholesterol Education's Program's recommendations, and implications of the "missing" high-density lipoprotein cholesterol in cardiac rehabilitation programs. American Journal of Cardiaology 1991; 68:1087-8.

Lefkowitz R J, Willerson J T. Prospects for cardiovascular research. Journal of the American Medical Association. 2001 Feb. 7; 285(5):581-7. PMID: 11176863

Miyamoto Y, Koh Y H, Park Y S, Fujiwara N, Sakiyama H, Misonou Y, Ookawara T, Suzuki K, Honke K, Taniguchi N. Oxidative stress caused by inactivation of glutathione peroxidase and adaptive responses. Biol Chem. 2003 April; 384(4):567-74. PMID: 12751786

Madamanchi N R, Hakim Z S, Runge M S. Oxidative stress and vascular disease. Arteriosclerosis Thrombosis Vascular Biology. 2005 January; 25(1):29-38. Epub 2004 Nov. 11. Review. PMID: 15539615

Meisinger C, Baumert J, Khuseyinova N, Loewel H, Koenig W. Plasma oxidized low-density lipoprotein, a strong predictor for acute coronary heart disease events in apparently healthy, middle-aged men from the general population. Circulation. 2005 Aug. 2; 112(5):651-7. Epub 2005 Jul. 25. PMID: 16043640

Molin M, Schutz A, Skerfving S, Sallsten G. Mobilized mercury in subjects with varying exposure to elemental mercury vapour. International Archives Occupational Environmental Health. 1991; 63(3):187-92. PMID: 1917069

Navab M, Anantharamaiah G M, Reddy S T, Van Lenten B J, Ansell B J, Fogelman A M. Mechanisms of disease: proatherogenic HDL—an evolving field. Nature clinical practice. Endocrinology & metabolism. 2006 September; 2(9): 504-11. Review. PMID: 16957764

Opara E C. Oxidative stress, micronutrients, diabetes mellitus and its complications. Journal of the Royal Society of Health. 2002 March; 122(1):28-34. PMID: 11989140

Penckofer S, Schwertz D, Florczak K. Oxidative stress and cardiovascular disease in type 2 diabetes: the role of antioxidants and pro-oxidants. J Cardiovascular Nursing. 2002 January; 16(2):68-85 PMID: 11800069

Salonen J T, Seppanen K, Nyyssonen K, Korpela H, Kauhanen J, Kantola M, Tuomilehto J, Esterbauer H, Tatzber F, Salonen R. Intake of mercury from fish, lipid peroxidation, and the risk of myocardial infarction and coronary, cardiovascular, and any death in Eastern Finnish men. Circulation. 1995; 91: 645-655 PMID: 7828289

Santangelo F. The regulation of sulphurated amino acid junctions: fact or fiction in the field of inflammation? Amino Acids. 2002; 23(4):359-65. Review. PMID: 12436203

Seppanen K, Soininen P, Salonen J T, Lotjonen S, Laatikainen R. Does mercury promote lipid peroxidation? An in vitro study concerning mercury, copper, and iron in peroxidation of low-density lipoprotein. Biol Trace Elem Res. 2004 November; 101(2):117-32. PMID: 15557676

Stocker R, Keaney J F Jr. Role of Oxidative Modifications in Atherosclerosis. Physiological Review, Oct. 1, 2004; 84(4): 1381-1478. PMID: 15383655 http://physrev.physiology.org/cgi/content/full/84/4/1381

Stohs S J, Bagchi D. Oxidative mechanisms in the toxicity of metal ions. Free Radic Biol Med. 1995 February; 18(2): 321-36. Review. PMID: 7744317

Tagliabue M, Pinach S, Di Bisceglie C, Brocato L, Cassader M, Bertagna A, Manieri C, Pescarmona G P. Glutathione levels in patients with erectile dysfunction, with or without diabetes mellitus. International Journal Andrology. 2005 June; 28(3):156-62. PMID: 15910541

Tappia P S, Dent M R, Dhalla N S. Oxidative stress and redox regulation of phospholipase D in myocardial disease. Free Radical Biology Medicine. 2006 Aug. 1; 41(3):349-61. Epub 2006 Apr. 4. PMID: 16843818

Virtanen J K, Voutilainen S, Rissanen T H, Mursu J, Tuomainen T P, Korhonen M J, Valkonen V P, Seppanen K, Laukkanen J A, Salonen J T. Mercury, fish oils, and risk of acute coronary events and cardiovascular disease, coronary heart disease, and all-cause mortality in men in eastern Finland. Arteriosclerosclerosis Thrombosis and Vascular Biology. 2005 January; 25(1):228-33. Epub 2004 Nov. 11. PMID: 15539625

Waynberg J, Brewer S. Effects of Herbal vX on libido and sexual activity in premenopausal and postmenopausal women. Advances in therapy, 2000 September-October; 17(5):255-62. PMID: 11186145

Que L G, Liu L, Yan Y, Whitehead G S, Gavett S H, Schwartz D A, Stamler J S. Protection from experimental asthma by an endogenous bronchodilator. Science. 2005 Jun. 10; 308 (5728):1618-21. Epub 2005 May 26. PMID: 15919956

Valko M, Morris H, Cronin M. Metals, Toxicity and Oxidative Stress. Current Medicinal Chemistry, Volume 12, Number 10, May 2005, pp. 1161-1208(48)

Zettler M E, Prociuk M A, Austria J A, Massaeli H, Zhong G, Pierce G N. OxLDL stimulates cell proliferation through a general induction of cell cycle proteins. American Journal Physiology Heart Circulation Physiology. 2003 February; 284(2):H644-53. PMID: 12529257

What is claimed is:

1. A pharmaceutical composition for treatment of vascular disease in a mammalian patient, comprising:
   reduced glutathione in a liposomal formulation capable of administration orally, dermally or mucosally, where the concentration of reduced glutathione in the entrapped aqueous space of the liposomes is at least 123 mM; and
   a cholesterol lowering agent chosen from the group of drugs known as statins.

* * * * *